(12) United States Patent
Ando et al.

(10) Patent No.: US 11,690,585 B2
(45) Date of Patent: Jul. 4, 2023

(54) RADIATION IMAGE DISPLAY APPARATUS AND RADIATION IMAGING SYSTEM

(71) Applicant: Konica Minolta, Inc., Tokyo (JP)

(72) Inventors: Takanori Ando, Hachioji (JP); Yuuichi Nishijima, Mitaka (JP); Kenichi Yanagisawa, Kokubunji (JP); Ichirou Hamamoto, Fuchu (JP)

(73) Assignee: KONICA MINOLTA, INC., Tokyo (JP)

(*) Notice: Subject to any disclaimer, the term of this patent is extended or adjusted under 35 U.S.C. 154(b) by 7 days.

(21) Appl. No.: 17/464,094

(22) Filed: Sep. 1, 2021

(65) Prior Publication Data

US 2021/0398284 A1 Dec. 23, 2021

Related U.S. Application Data

(63) Continuation of application No. 16/380,021, filed on Apr. 10, 2019, now Pat. No. 11,138,725.

(30) Foreign Application Priority Data

Apr. 11, 2018 (JP) .................... 2018-076006

(51) Int. Cl.
*G06K 9/00* (2022.01)
*A61B 6/00* (2006.01)
*G06T 7/00* (2017.01)

(52) U.S. Cl.
CPC ............ *A61B 6/463* (2013.01); *A61B 6/5211* (2013.01); *G06T 7/0012* (2013.01); *G06F 2218/10* (2023.01)

(58) Field of Classification Search
CPC ..... G06T 7/0012; A61B 6/5211; A61B 6/465; A61B 6/486; A61B 6/50; A61B 6/5217;
(Continued)

(56) References Cited

U.S. PATENT DOCUMENTS 11,138,725 B2 * 10/2021 Ando ................ A61B 6/5217
2001/0021263 A1 9/2001 Oosawa
(Continued)

FOREIGN PATENT DOCUMENTS

EP 2829231 A1 1/2015
JP 2006503632 A 2/2006
(Continued)

OTHER PUBLICATIONS

JPO Notice of Reasons for Refusal for corresponding JP Application No. 2018-076006; dated May 10, 2022.
(Continued)

*Primary Examiner* — Samir A Ahmed
(74) *Attorney, Agent, or Firm* — Cantor Colburn LLP

(57) ABSTRACT

A radiation image display apparatus that constitutes a radiation imaging system includes a displayer and a hardware processor that acquires image data of a dynamic image constituted of a plurality of frame images, image data of an analysis dynamic image obtained by applying predetermined image processing to the image data of the dynamic image and image data of a related dynamic image which is related to the dynamic image or the analysis dynamic image respectively, and causes the displayer to display the related dynamic image together with the dynamic image and the analysis dynamic image.

9 Claims, 43 Drawing Sheets

(58) Field of Classification Search
CPC ...... A61B 6/463; G06K 9/0053; G06V 10/40; G16H 50/20
See application file for complete search history.

(56) References Cited

U.S. PATENT DOCUMENTS

| | | | |
|---|---|---|---|
| 2012/0130238 A1* | 5/2012 | Muraoka | A61B 6/4233 600/436 |
| 2013/0156267 A1 | 6/2013 | Muroaka et al. | |
| 2015/0073257 A1* | 3/2015 | Muraoka | A61B 6/5264 600/407 |
| 2015/0077432 A1 | 3/2015 | Toyama et al. | |
| 2016/0098836 A1 | 4/2016 | Yamato et al. | |
| 2016/0120491 A1 | 5/2016 | Shimamura et al. | |
| 2016/0031007 A1 | 10/2016 | Ishida | |
| 2016/0350923 A1 | 12/2016 | Muraoka et al. | |
| 2017/0020470 A1 | 1/2017 | Tezuka et al. | |
| 2017/0025158 A1 | 1/2017 | Miyake et al. | |
| 2017/0367623 A1* | 12/2017 | Nakazawa | A61B 5/1128 |

FOREIGN PATENT DOCUMENTS

| | | |
|---|---|---|
| JP | 2008301984 A | 12/2008 |
| JP | 2009273671 A | 11/2009 |
| JP | 2012110400 A | 6/2012 |
| JP | 2016002251 A | 1/2016 |
| JP | 2017018681 A | 1/2017 |
| JP | 2017200565 A | 11/2017 |
| WO | 2014203938 A1 | 12/2014 |
| WO | 2015157067 A1 | 10/2015 |

OTHER PUBLICATIONS

JPO Notice of Reasons for Refusal for corresponding JP Application No. JP2018-076006; dated Dec. 7, 2021.

USPTO Non-Final Office Action for corresponding U.S. Appl. No. 16/380,021; dated Feb. 23, 2021.

* cited by examiner

RADIATION IMAGE DISPLAY APPARATUS AND RADIATION IMAGING SYSTEM

CROSS REFERENCES TO RELATED APPLICATIONS

The present application is a continuation application of U.S. patent application Ser. No. 16/380,021, filed on Apr. 10, 2019. Priority under 35 U.S.C. § 119 is hereby claimed from Japanese Application No. 2018-076006, filed on Apr. 11, 2018, the disclosures of which are both incorporated herein by reference.

BACKGROUND

Technological Field

The present invention relates to a radiation image display apparatus and a radiation imaging system.

Description of the Related Art

One of radiograph imaging techniques is moving image capturing (also referred to as "serial imaging").
In moving image capturing, a plurality of frame images are repeatedly generated in a predetermined cycle (e.g., 15 times per second). By playing back (sequentially displaying a plurality of frame images) dynamic images obtained through moving image capturing on a display apparatus, it is possible to observe operation of an imaging target region (e.g., lung field).
In recent years, by applying various kinds of image processing as described, for example, in National Publication of International Patent Application No. 2017-510427, Japanese Patent Laid-Open No. 2016-002251, Japanese Patent Laid-Open No. 2009-273671 or Japanese Patent Laid-Open No. 2017-200565 to image data of dynamic images, it is possible to improve viewability of an imaging target region or track all details of operation of the imaging target region.

SUMMARY

Such moving image capturing is often conducted for one subject a plurality of times at a certain interval of days to get a follow-up observation of the subject. For this reason, a diagnosis using dynamic images requires comparison of a dynamic image obtained through new image capturing with an analysis dynamic image obtained by applying image processing to a dynamic image obtained through past image capturing or comparison of an analysis dynamic image obtained by applying image processing to a dynamic image obtained through new image capturing with a past analysis dynamic image or the like.
However, since there are several types of image processing, the number of dynamic images to be compared generally tends to increase. Furthermore, conventional display apparatuses necessitate switching of display to find out past analysis dynamic images to be compared or to compare a comparison source dynamic image with a comparison target analysis dynamic image, and so performing comparison requires time and effort.
It is an object of the present invention to facilitate comparison between a comparison source dynamic image and a comparison target dynamic image.
To achieve at least one of the abovementioned objects, according to a first aspect of the present invention, a radiation image display apparatus reflecting one aspect of the present invention comprises a displayer and a hardware processor that acquires image data of a dynamic image constituted of a plurality of frame images, image data of an analysis dynamic image obtained by applying predetermined image processing to the image data of the dynamic image and image data of a related dynamic image which is related to the dynamic image or the analysis dynamic image respectively, and causes the displayer to display the related dynamic image together with the dynamic image and the analysis dynamic image.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.
FIG. 7 shows an example of a display screen of the radiation image display apparatus in FIG. 2.

FIG. 21 shows an example of a display screen of the radiation image display apparatus according to the associated technique;

FIG. 22 shows an example of a display screen of the radiation image display apparatus according to the associated technique;

FIG. 25 shows an example of a display screen of the radiation image display apparatus according to the associated technique;

FIG. 27 shows an example of a display screen of the radiation image display apparatus according to the associated technique;

Figure 32:
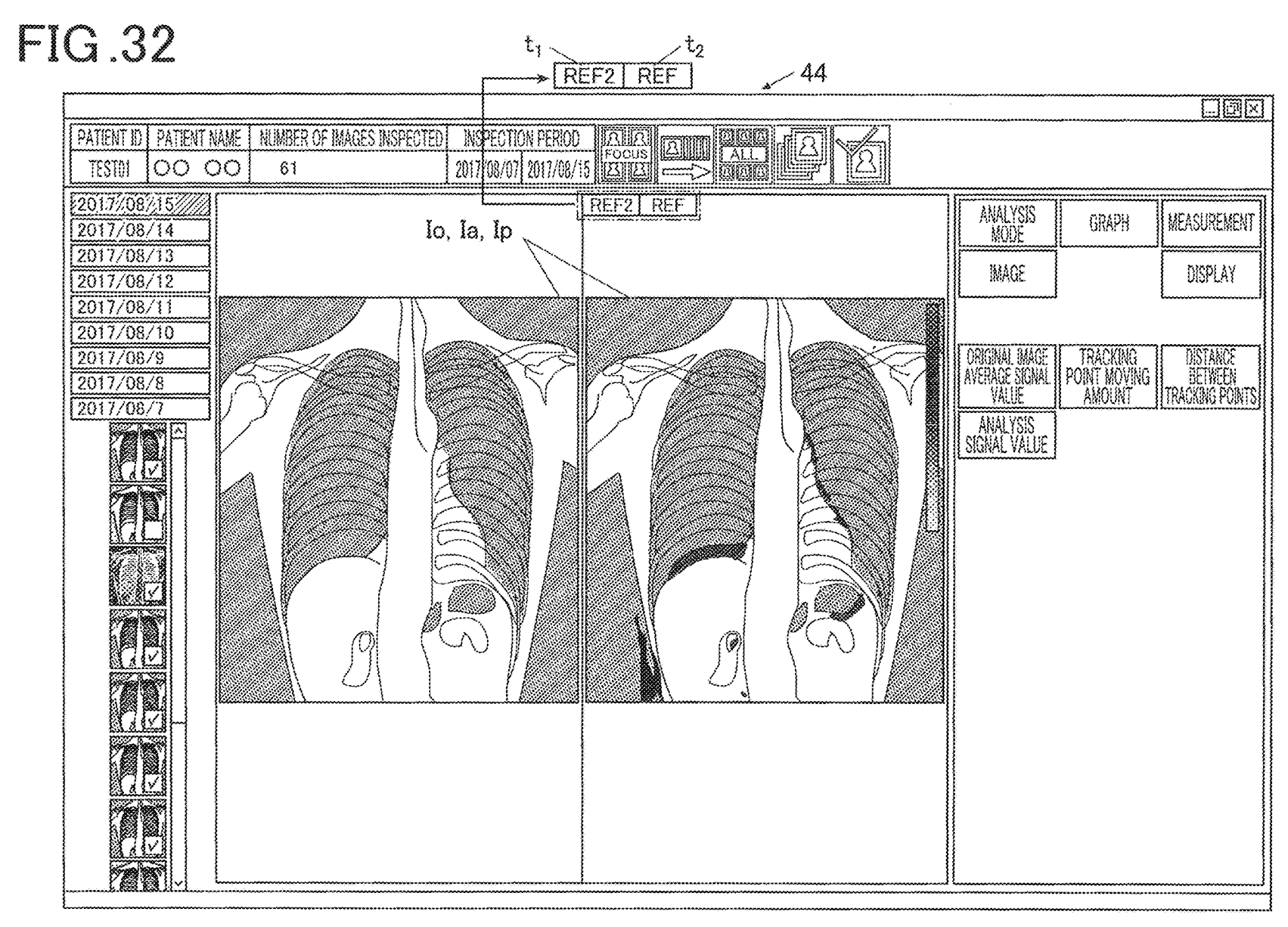

FIG. 32 shows an example of a display screen of the radiation image display apparatus according to the associated technique;

FIG. 35 shows an example of a display screen of the radiation image display apparatus according to the associated technique;

FIG. 36 shows an example of a display screen of the radiation image display apparatus according to the associated technique;

FIG. 44 shows an example of a display screen of the radiation image display apparatus according to the associated technique.

DETAILED DESCRIPTION OF EMBODIMENTS

Hereinafter, one or more embodiment of the present invention will be described with reference to the drawings. However, the scope of the invention is not limited to the disclosed embodiments.

[Radiation Imaging System]

Figure 1:
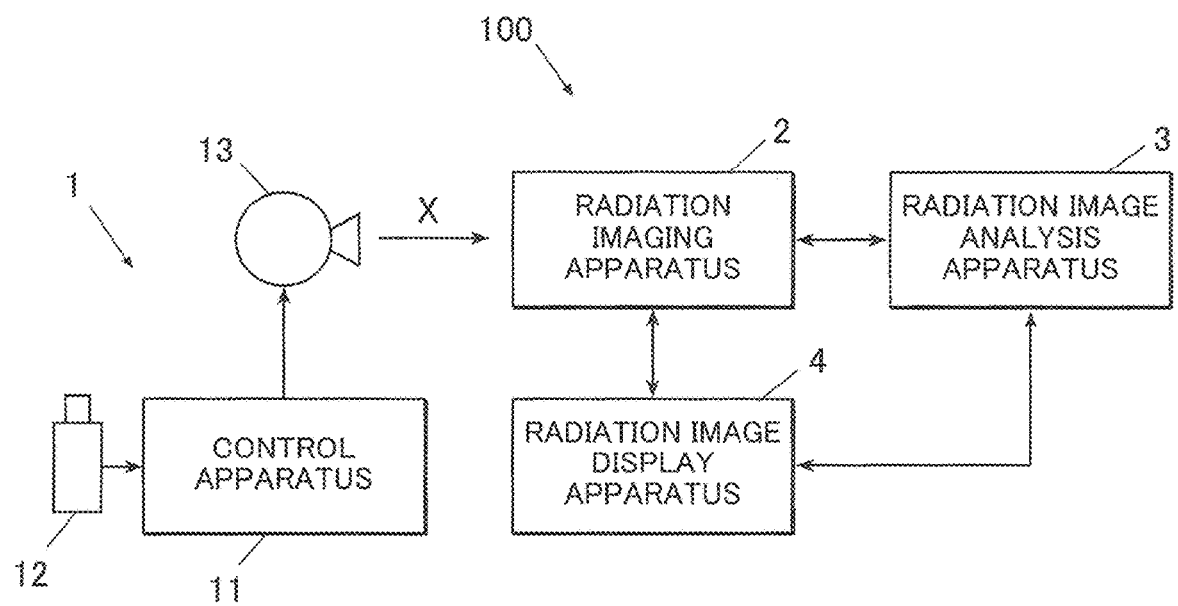
FIG. 1 is a block diagram illustrating a schematic configuration of a radiation imaging system according to an embodiment of the present invention.

A configuration of a radiation imaging system (hereinafter referred to as an "imaging system 100") according to the present embodiment will be described first. FIG. 1 is a block diagram illustrating a schematic configuration of the imaging system 100.

As shown in FIG. 1, the imaging system 100 of the present embodiment is configured to include a radiation irradiation apparatus (hereinafter referred to as an "irradiation apparatus 1"), a radiation imaging apparatus (hereinafter referred to as an "imaging apparatus 2"), a radiation image analysis apparatus (hereinafter referred to as an "analysis apparatus 3") and a radiation image display apparatus (hereinafter referred to as a "display apparatus 4").

The irradiation apparatus 1 is configured to include a control apparatus 11, an exposure switch 12, and a radiation source (bulb) 13.

The control apparatus 11 is configured to be able to apply a voltage corresponding to a preset radiation exposure condition (tube voltage, tube current, irradiation time (mAs value) or the like) to the radiation source 13 based on pressing of the exposure switch 12.

The radiation source 13 includes a rotating anode and a filament, which are not shown, or the like. The radiation source 13 is configured such that when a voltage is applied from the control apparatus 11, the filament irradiates the rotating anode with an electron beam corresponding to the applied voltage and the rotating anode generates radiation (X-rays or the like) with a dose corresponding to an intensity of the electron beam.

The irradiation apparatus 1 is configured to be able to repeatedly radiate pulse radiation having a predetermined time width in a predetermined cycle based on one imaging operation (pressing of the exposure switch 12).

The irradiation apparatus 1 is configured to be able to change the orientation of a radiation irradiation port of the radiation source 13 and irradiate a subject in an upright position or a subject in a lying position with radiation (carrying out both upright position imaging and lying position imaging).

Note that the irradiation apparatus 1 may be of a type fixed to an imaging chamber or of a mobile type provided with wheels.

The imaging apparatus 2 is configured to be able to repeatedly generate image data of a radiation image based on the radiation received from the irradiation apparatus 1 in a predetermined cycle and is connected with the analysis apparatus 3 and the display apparatus 4 so as to be communicable therewith by wired or wireless means.

Furthermore, the imaging apparatus 2 is also configured to include a radiation detector and a reader or the like, which are not shown.

The radiation detector may include a substrate on which a plurality of pixels are two-dimensionally arrayed, each pixel including a radiation detection element that directly or indirectly generates a quantity of charge corresponding to the dose of radiation by receiving radiation from outside and a switch element that can switch between ON-state in which conduction between the radiation detection element and wiring provided between each radiation detection element and wiring is enabled and OFF-state in which conduction is disabled, and any publicly known conventional radiation detector may be used.

That is, the imaging apparatus 2 may be a so-called indirect type apparatus provided with a scintillator, detecting light emitted from the scintillator by receiving radiation or may be a so-called direct type apparatus directly detecting radiation without interposing a scintillator.

The reader may be configured to be able to read a quantity of charge accumulated in a plurality of radiation detection elements as a signal value and generate image data of a radiation image based on each signal value, and any publicly known conventional reader can be used.

The analysis apparatus 3 is configured to be able to apply various kinds of image processing to image data using a PC, a portable terminal or a dedicated apparatus and generate image data of a plurality of types of analysis dynamic images, and is connected with the imaging apparatus 2 and the display apparatus 4 so as to be communicable by wired or wireless means.

The display apparatus 4 is constructed of a PC, a portable terminal or a dedicated apparatus, and is connected with the imaging apparatus 2 and the display apparatus 4 so as to be communicable by wired or wireless means. Details of the display apparatus 4 will be described later.

By irradiating the subject disposed between the irradiation apparatus 1 and the imaging apparatus 2 with radiation from the irradiation apparatus 1, the imaging system 100 of the present embodiment configured in this way can perform radiation imaging of the subject.

Particularly, it is possible for the imaging apparatus 2 to capture dynamic images of the subject by repeatedly irradiating the subject with pulse radiation from the irradiation apparatus 1 and repeatedly generating dynamic images of the subject. Hereinafter, capturing dynamic images will be referred to as "moving image capturing" and each radiation image constituting a dynamic image will be referred to as a "frame image."

Furthermore, the imaging system 100 can also be used by being connected with a radiology information system (RIS), a picture archiving and communication system (PACS) (not shown) or the like.

Note that although a case has been shown in FIG. 1 where the analysis apparatus 3 and the display apparatus 4 are provided separately, the analysis apparatus 3 and the display apparatus 4 may be integrated as one unit. That is, the display apparatus 4 may incorporate the function of the analysis apparatus 3.

[Radiation Image Display Apparatus]

Figure 2:
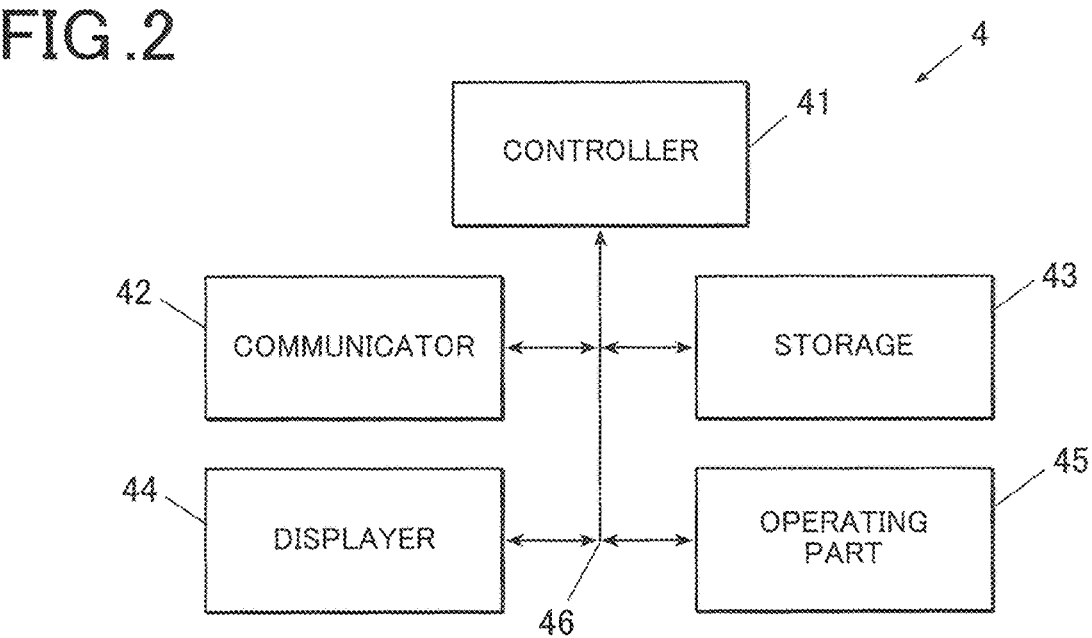
FIG. 2 is a block diagram illustrating a specific configuration of a radiation image display apparatus provided for the radiation imaging system in FIG. 1.

Next, details of the display apparatus 4 provided for the above imaging system 100 will be described. FIG. 2 is a block diagram illustrating a specific configuration of the display apparatus 4.

As shown in FIG. 2, the display apparatus 4 is provided with a controller 41, a communicator 42, a storage 43, a displayer 44, an operating part 45 and a bus 46 that connects the respective parts.

The controller 41 is constructed of a CPU (central processing unit), a RAM (random access memory) or the like. The CPU of the controller 41 reads various programs stored in the storage 43, develops the programs in the RAM, executes various types of processing according to the developed programs and controls the respective parts of the display apparatus 4 in a concentrated manner.

The communicator 42 is constructed of a wireless module or the like and can transmit various kinds of information (signals or data) to/from other apparatuses (imaging apparatus 2 and analysis apparatus 3 or the like) via a communication network such as a LAN (local area network), WAN (wide area network) or the Internet.

The storage 43 is constructed of a non-volatile semiconductor memory or a hard disk, and stores various programs executed by the controller 41 (including a program for performing imaging control processing which will be described later) or parameters or the like necessary to execute processing according to the program.

The displayer 44 is constructed of a monitor such as an LCD (liquid crystal display) or CRT (cathode ray tube) and displays images and various kinds of information according to an instruction of a display signal inputted from the controller 41.

The operating part 45 is constructed of a keyboard provided with cursor keys, numeric input keys and various types of function keys, a pointing device such as a mouse, and a touch panel overlaid on a display screen of the displayer 44 or the like, configured to be operable by the user.

The operating part 45 outputs a command signal based on an operation executed by the user to the controller 41.

The controller 41 of the display apparatus 4 configured in this way has functions as shown below according to the program stored in the storage 43.

More specifically, the controller 41 has functions of acquiring image data of a dynamic image constituted of a plurality of frame images, image data of an analysis dynamic image Ia obtained by applying predetermined image processing to the image data of the dynamic image, and image data of a related dynamic image Ip which is related to an original dynamic image Io or the analysis dynamic image Ia.

The image data of the original dynamic image Io or the image data of the analysis dynamic image Ia may be acquired by receiving the image data from another apparatus (e.g., analysis apparatus 3) via the communicator 42 or may be acquired by calling image data stored in the storage 43.

Here, "image processing" includes a plurality of types of processing such as specific component differential processing, frequency emphasis processing, specific component tracking processing, specific signal change amount extraction processing, specific similar waveform pattern extraction processing or the like. Only one type of processing may be applied or a plurality of kinds of processing may be applied in combination.

The specific component differential processing is processing of improving viewability of an area other than a specific area by reducing a signal value of a specific area (e.g., rib or clavicle in the lung field) in an imaging target region.

The frequency emphasis processing is processing of defining a specific area by emphasizing a frequency of an edge of the specific area in an imaging target region.

The specific component tracking processing is processing of calculating a moving amount or speed of a specific area (e.g., diaphragm) in an imaging target region or calculating a distance between two different specific areas (e.g., between pulmonary apex and diaphragm).

The specific signal change amount extraction processing is processing of visualizing a change amount of a signal value by different colors.

The specific similar waveform pattern extraction processing is processing of visualizing a similarity level in a specific signal change by different colors.

In the present embodiment, in addition to the aforementioned processing, it is also possible to apply processing of visualizing a total amount of signal changes in image capturing by displaying a difference between an integrated image of a maximum signal value and an integrated image of a minimum signal value.

More specifically, an identical coordinate is specified for all the frame images, and a maximum signal value and a minimum signal value are calculated from among signal values of the respective frame images at the coordinate. Then, a difference between a frame image having the maximum signal value and a frame image having the minimum signal value is displayed as one image.

By so doing, when there is a signal change, in the case of the diaphragm, for example, it is possible to visualize a difference when the diaphragm ascends and the diaphragm descends.

Furthermore, the "related dynamic image" mainly refers to a dynamic image or analysis dynamic image obtained by capturing an image of the same subject at least once in the past.

The image data of the related dynamic image may also be acquired by receiving the image data from another apparatus (imaging apparatus 2 or analysis apparatus 3) via the communicator 42 or may be acquired by calling the image data stored in the storage 43.

Note that instead of acquiring only one of the related dynamic image Ip related to the original dynamic image Io and the related dynamic image Ip related to the analysis dynamic image Ia, both of the related dynamic image Ip related to the original dynamic image Io and the related dynamic image Ip related to the analysis dynamic image Ia may be acquired.

Furthermore, the controller 41 has a function of causing the displayer 44 to display related dynamic images together with the original dynamic image Io and the analysis dynamic image Ia.

Figure 3:
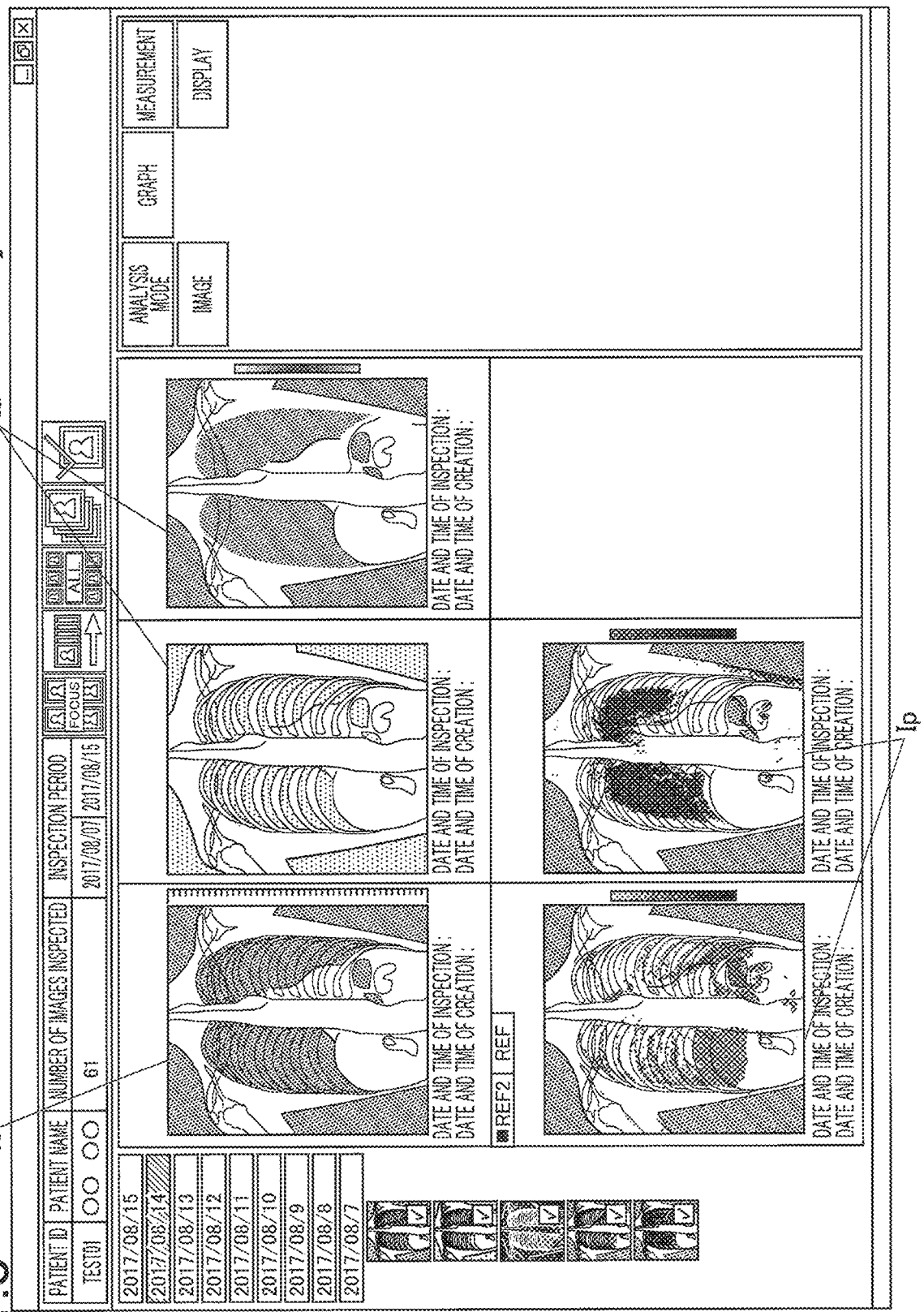
FIG. 3 shows an example of a display screen of the radiation image display apparatus in FIG. 2.

More specifically as shown, for example, in FIG. 3, in addition to the original dynamic image Io, various types of analysis dynamic images Ia obtained by applying various types of image processing to the original dynamic image Io can be displayed in a list. In this case, some of the original dynamic image Io or four types of analysis dynamic images Ia are related dynamic images Ip.

Note that the controller 41 according to the present embodiment also has functions as shown below in addition to the aforementioned function.

More specifically, the controller 41 has a function of causing the displayer 44 to display the related dynamic images Ip arranged in time series.

Figure 4:
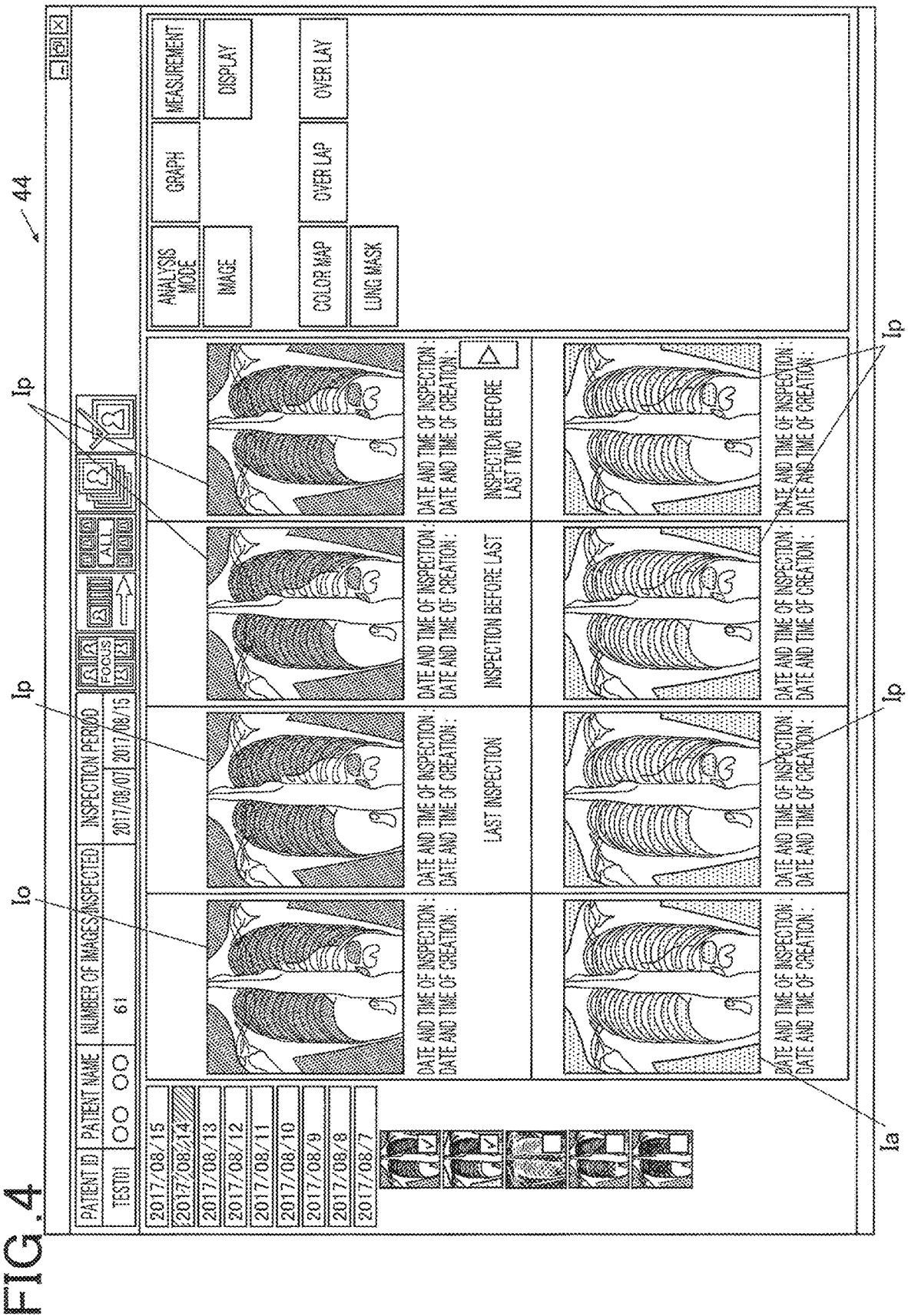
FIG. 4 shows an example of a display screen of the radiation image display apparatus in FIG. 2.
Figure 5:
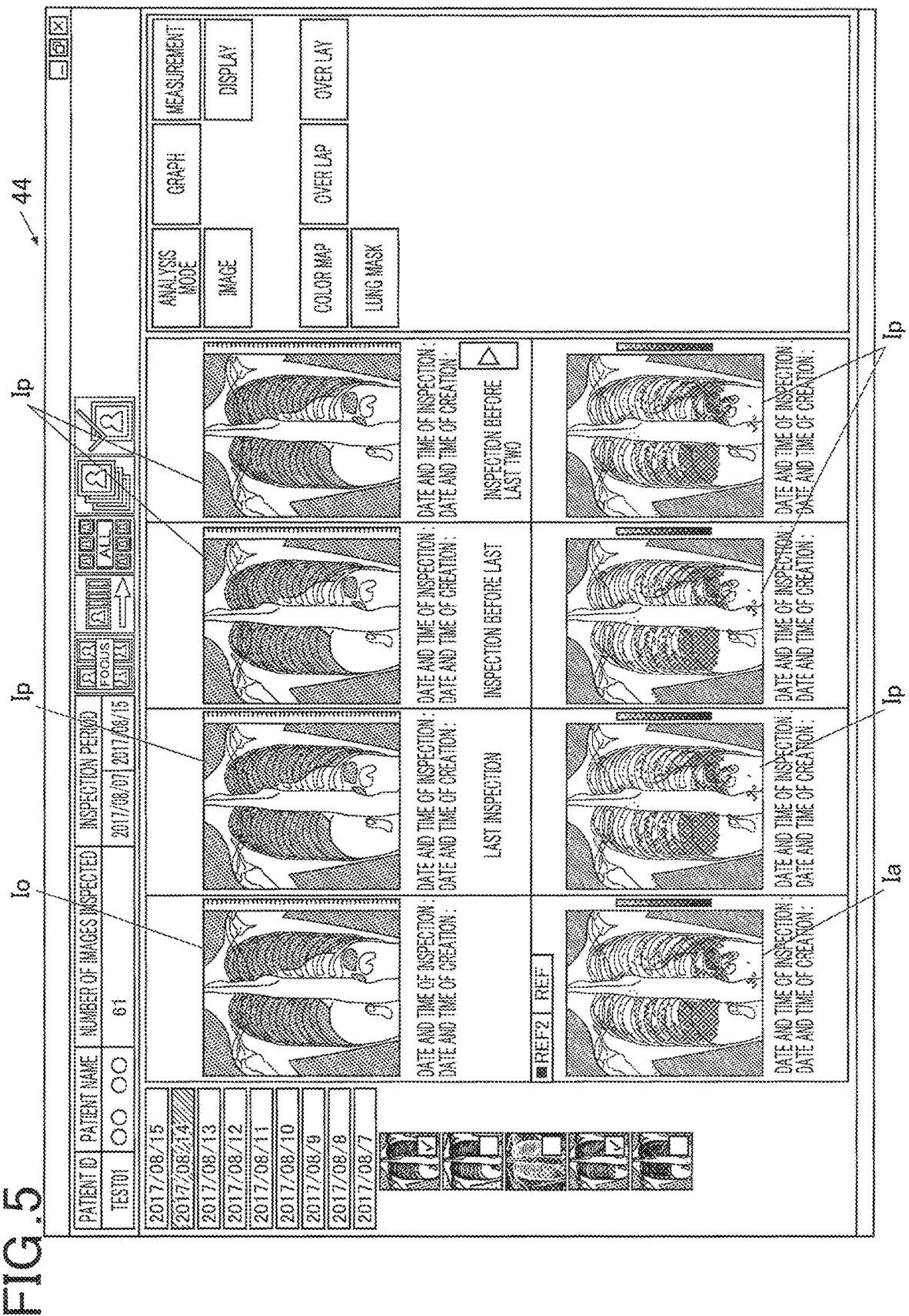
FIG. 5 shows an example of a display screen of the radiation image display apparatus in FIG. 2.

More specifically, as shown in FIG. 4 and FIG. 5, the original dynamic image Io and the analysis dynamic image Ia obtained through most recent image capturing, and original dynamic images and analysis dynamic images obtained through past image capturing are displayed arranged, for example, from newest to oldest. In this case, the past original dynamic images and past analysis dynamic images are the related dynamic images Ip.

Furthermore, in this case, the original dynamic image Io and the related dynamic images Ip in an upper row are dynamic images of the same type, and the analysis dynamic image Ia and the related dynamic images Ip in a lower row are also dynamic images of the same type.

Note that although FIG. 4 shows a case where in addition to the analysis dynamic image Ia, the corresponding original dynamic image Io is also displayed together, another analysis dynamic image Ia may also be displayed together or only one type of analysis dynamic image Ia may be displayed.

Furthermore, the controller 41 may be provided with a function of displaying a plurality of types of analysis dynamic images obtained by applying a plurality of types of image processing, one type at a time, superimposed on one another, in addition to the function of applying the aforementioned plurality of types of image processing in combination. In this case, the controller 41 may be further provided with a function of performing alpha blending (transmission designation).

Furthermore, the controller 41 has a function of switching display of the displayer 44 so that related dynamic images Ip which have not been displayed so far are displayed based on operation performed on the operating part 45 in the case where a number of related dynamic images Ip that cannot be displayed at a time on the displayer 44 are acquired.

Figure 6:
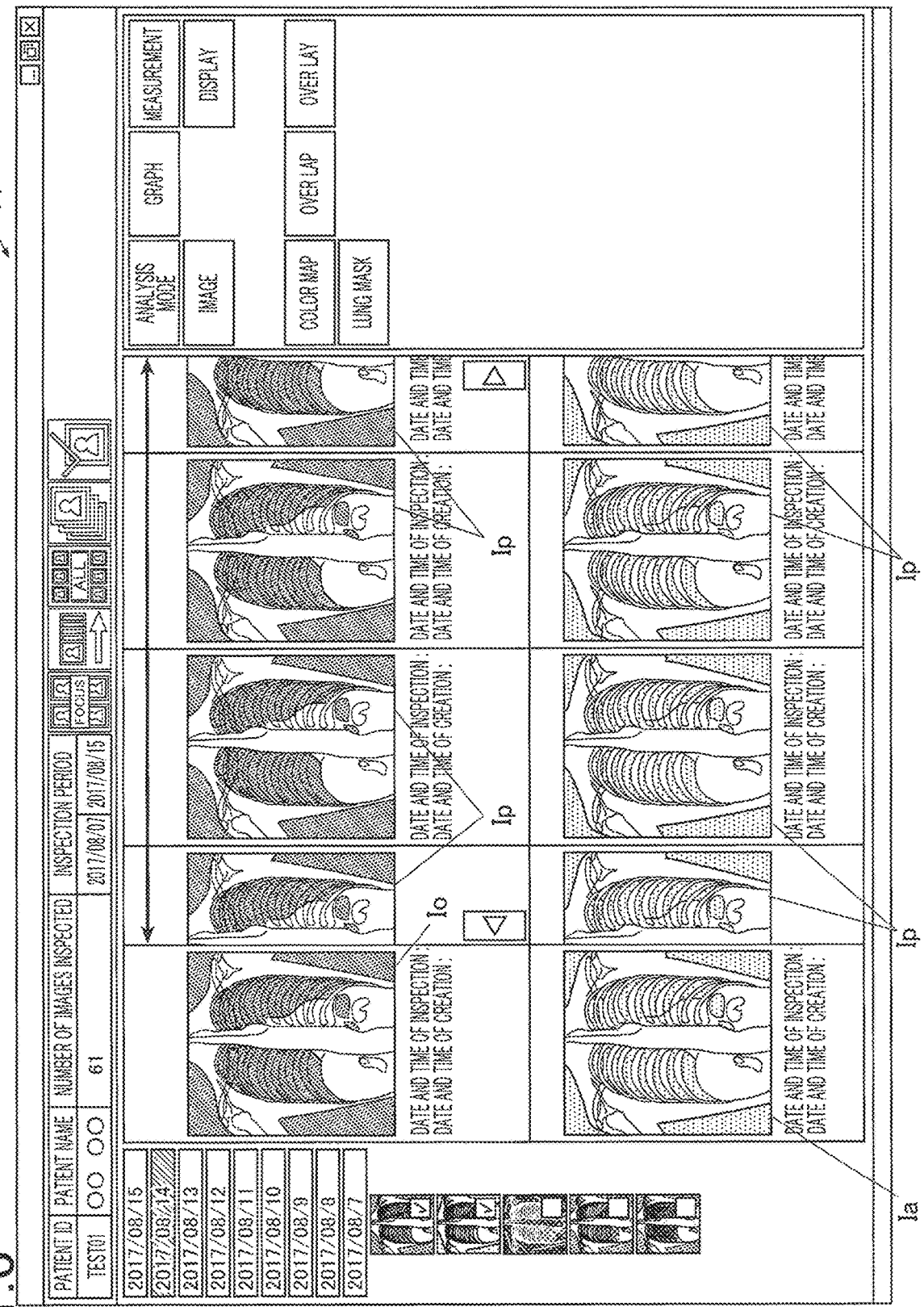
FIG. 6 shows an example of a display screen of the radiation image display apparatus in FIG. 2.

For example, when dynamic images are displayed in a form as shown in FIG. 6, the number of dynamic images that can be displayed at a time is limited to four. Thus, in the case where there are five or more acquired related dynamic images Ip, an image display region is scrolled or made to jump to an analysis dynamic image Ia which is hidden as shown in FIG. 6, by moving the mouse cursor while right-clicking, causing the mouse wheel to rotate, sliding a finger over the surface of a touch panel or clicking a predetermined location of the image display region.

Even when there are many dynamic images Io, Ia and Ip to be compared, having such a function can facilitate comparisons.

Furthermore, the controller 41 has a function of specifying some of the dynamic images Io, Ia and Ip displayed on the displayer 44 based on operation performed on the operating part 45.

More specifically, a dynamic image to be specified is specified by touching or clicking on the dynamic image. In the vicinity or adjacent to the specified dynamic image, a mark m (here, a pin pattern icon) may be displayed as shown in FIG. 7 or a frame f may be displayed as shown in FIG. 8.

The controller 41 is further provided with a function of switching display of regions in which dynamic images other than a specified dynamic image is displayed on the displayer 44.

Figure 7:
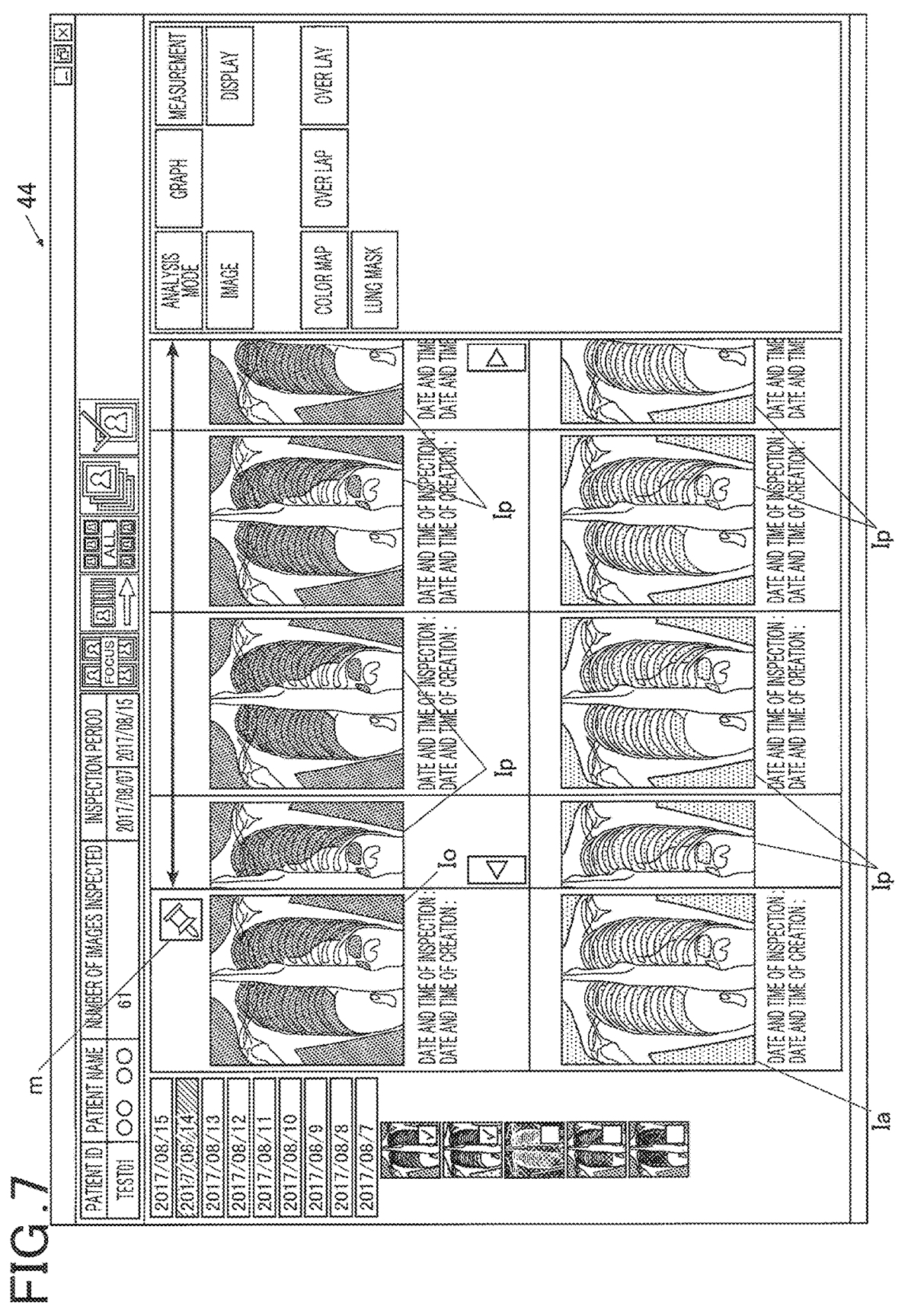
Figure 8:
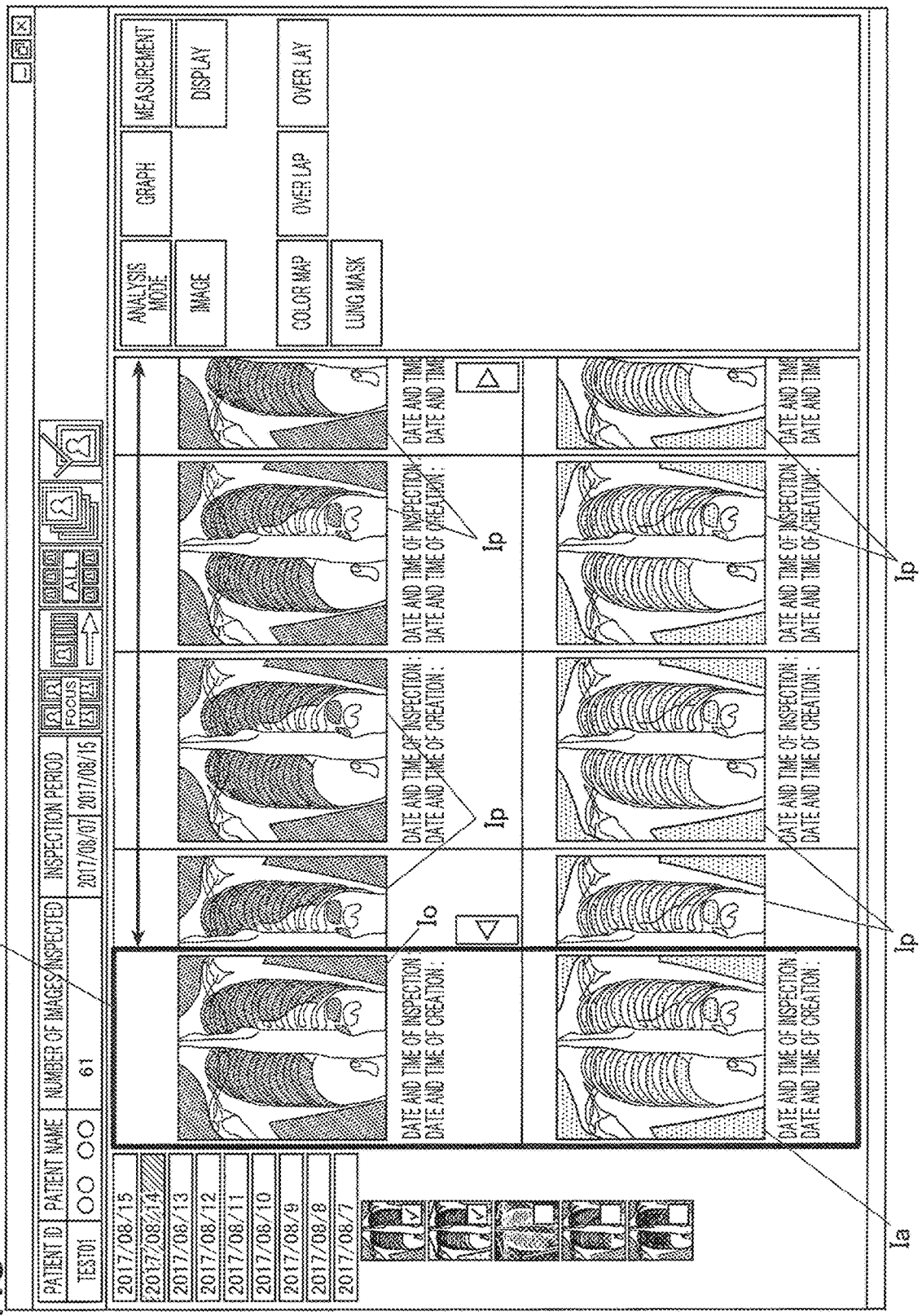
FIG. 8 shows an example of a display screen of the radiation image display apparatus in FIG. 2.

More specifically, as shown in FIG. 7 and FIG. 8, the specified dynamic image is fixedly displayed at a left end and other dynamic images are scroll-displayed in the region on the right side.

Having such a function can facilitate comparisons between a comparison source dynamic image and many comparison target dynamic images by specifying the comparison source dynamic image.

The controller 41 further has a function of associating a predetermined mark m or comment C with image capturing timings of the dynamic images Io, Ia and Ip or between the image capturing timings based on operation performed on the operating part 45.

Figure 9:
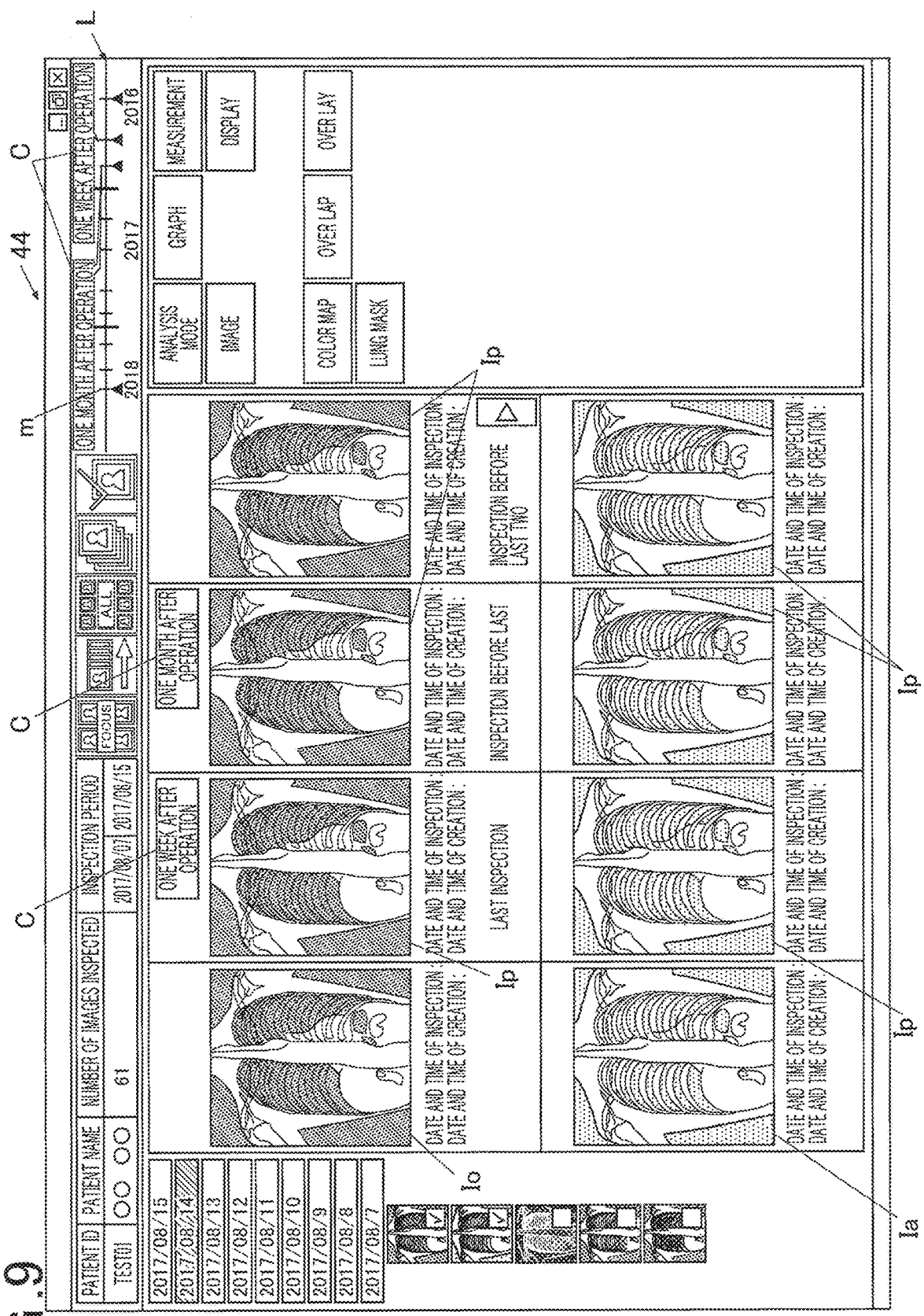
FIG. 9 shows an example of a display screen of the radiation image display apparatus in FIG. 2.

The associated comments C are displayed around the corresponding dynamic images as shown, for example, in FIG. 9.

Furthermore, the controller 41 can cause the displayer 44 to display the associated marks m or comments C arranged in time series and has a function of switching display of the displayer 44 upon selection of any one of the marks m or comments C based on operation performed on the operating part 45 so that a related dynamic image Ip associated with the selected mark m or comment C is displayed.

Figure 10:
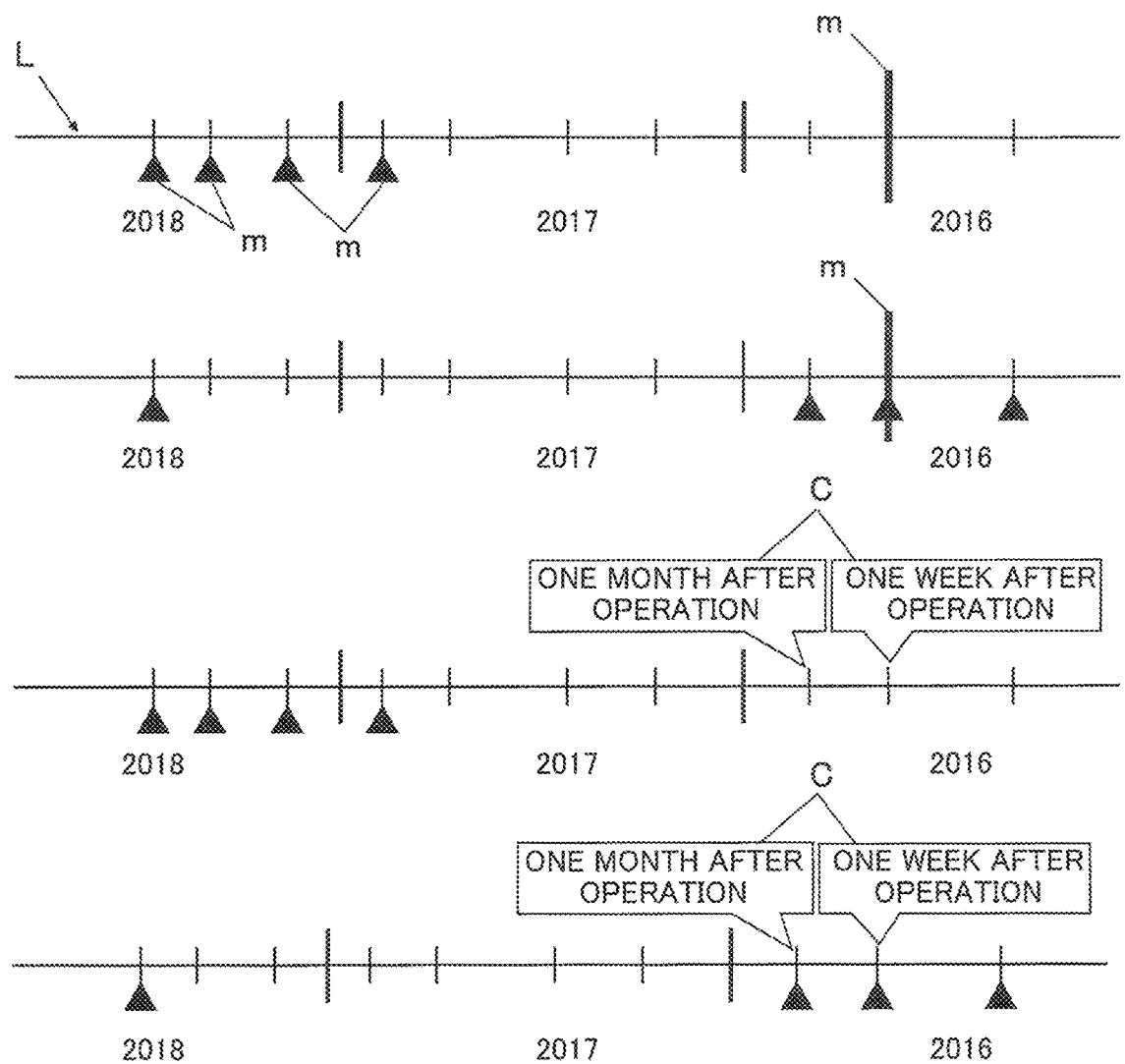
FIG. 10 shows an example of a sequence of marks or comments displayed by the radiation image display apparatus in FIG. 2.
Figure 11:
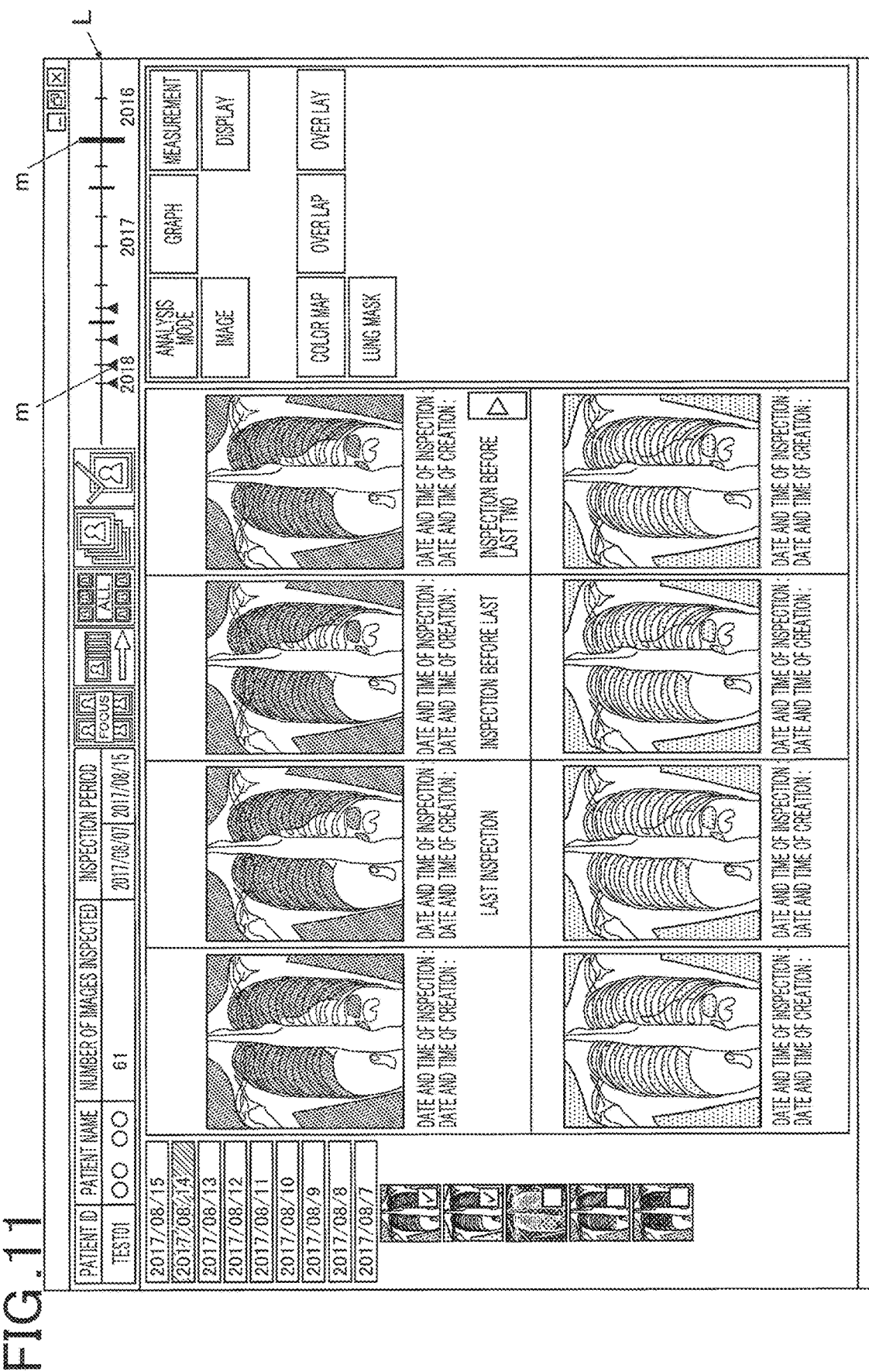
FIG. 11 shows an example of a display screen of the radiation image display apparatus in FIG. 2.

More specifically, as shown, for example, in FIG. 10, years and months indicated on a number line L can be displayed outside the image display region of the displayer 44 as shown in FIG. 9 and FIG. 11, and the marks m and comments C are displayed at positions corresponding to image capturing timings of the dynamic images with which the marks and comments are associated on the number line L. Any one of the marks m and comments C displayed on the number line is selected, and the corresponding dynamic images Io, Ia and Ip are thereby displayed.

Figure 12:
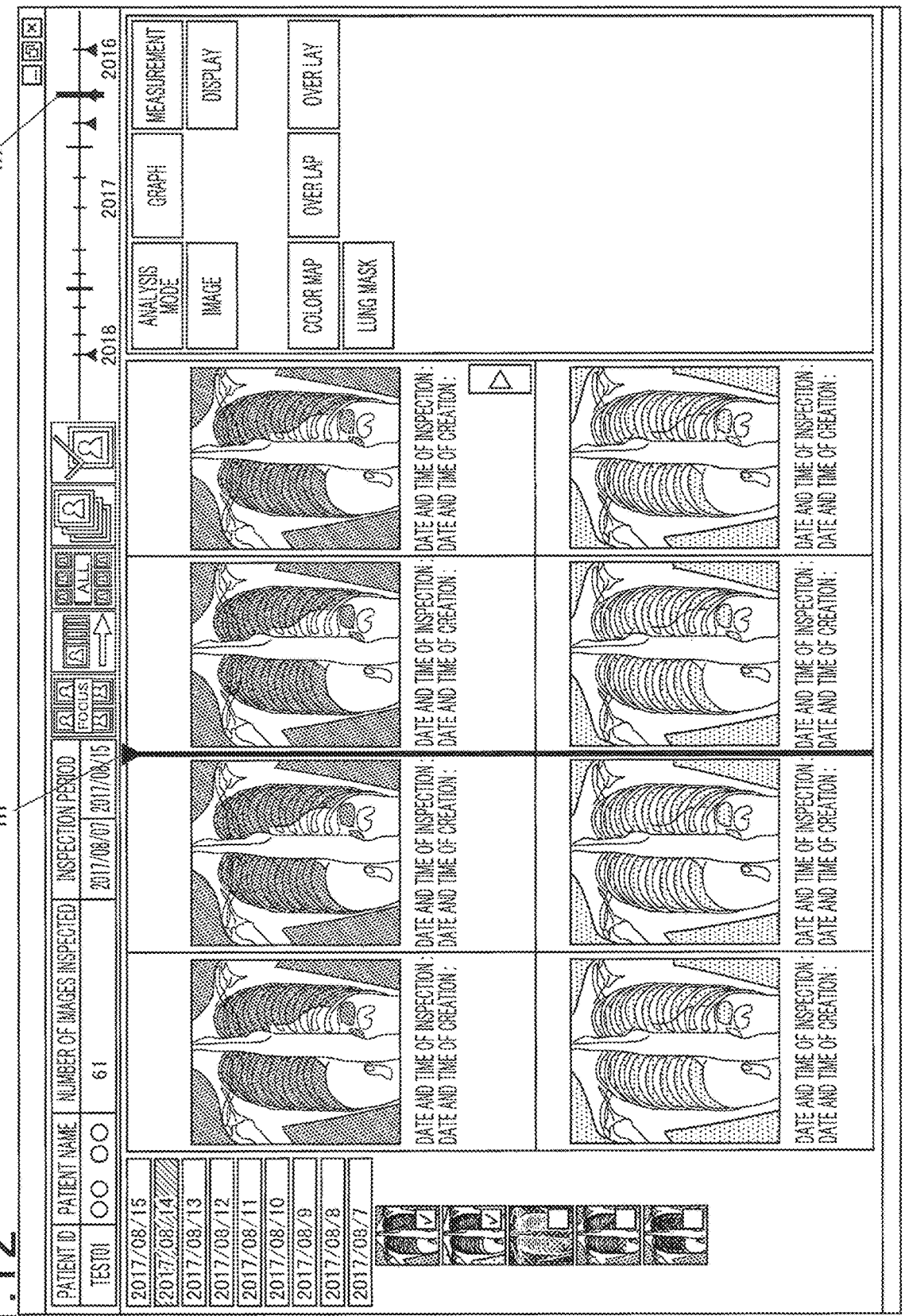
FIG. 12 shows an example of a display screen of the radiation image display apparatus in FIG. 2.

Note that the mark m may be substituted by a partition line as shown, for example, in FIG. 12, displayed on the number line L and also displayed between the dynamic images.

Having such a function makes it possible to easily grasp timings of image capturing in the past and easily display dynamic images at desired timings.

Furthermore, the controller 41 has a function of causing the displayer 44 to display a graph showing a relationship between a distance from the pulmonary apex to the diaphragm and the number of frame images in the analysis dynamic image Ia and the related dynamic image when the lung field is the imaging target region of the related dynamic image.

Figure 13:
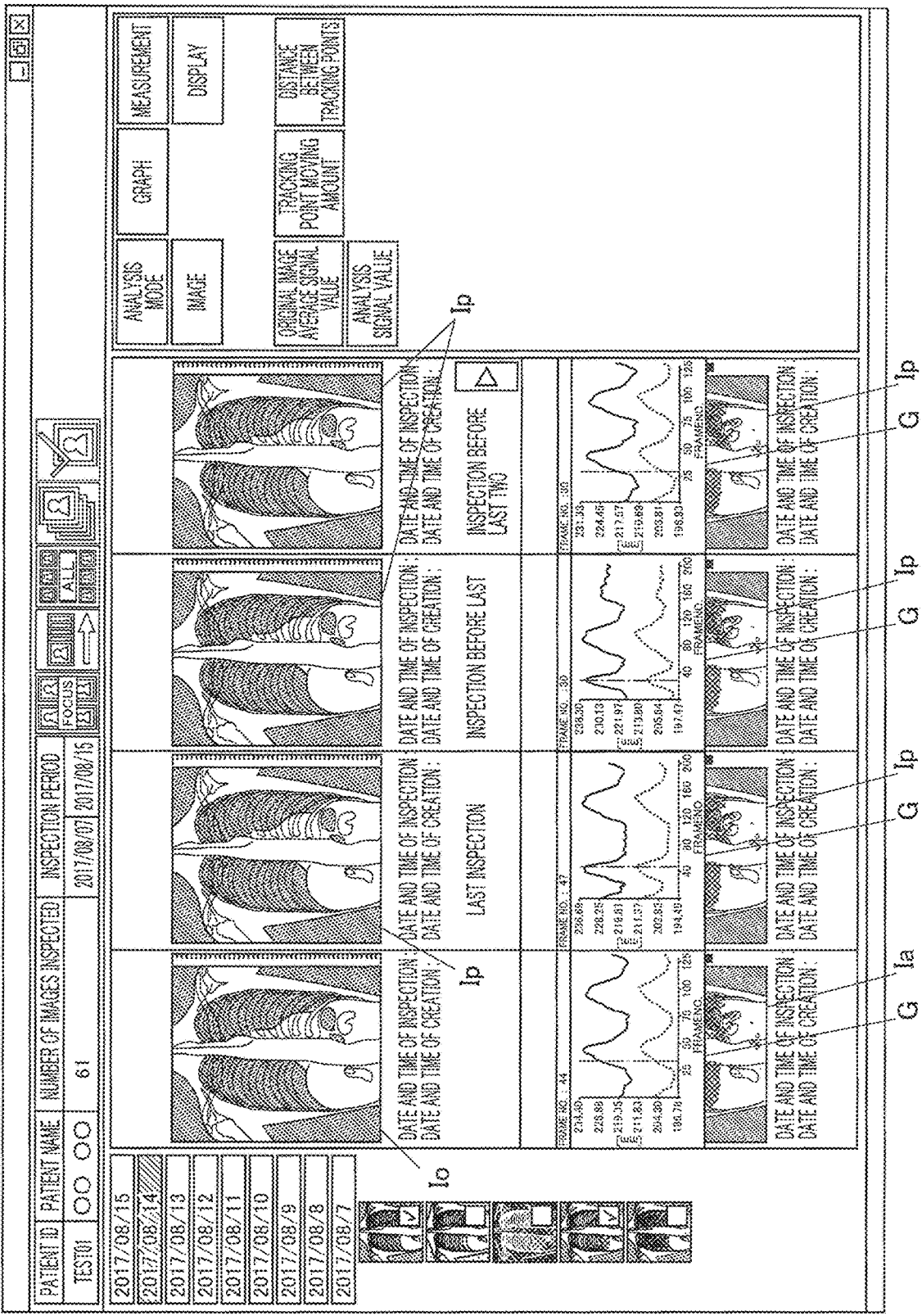
FIG. 13 shows an example of a display screen of the radiation image display apparatus in FIG. 2.

More specifically, as shown, for example, in FIG. 13, graphs G, the horizontal axis of which represents a frame number and the vertical axis of which represents a distance are displayed adjacent to the original dynamic image Io or each related dynamic image Ip.

Note that although a case has been illustrated in FIG. 13 where the graphs G are displayed in front of the corresponding analysis dynamic images Ia or related dynamic images Ip, the graphs G may be displayed in front of the original dynamic image Io so as not to shield the analysis dynamic images Ia or related dynamic images Ip, or the graphs G may be displayed at positions different from the image display region so as not to shield any dynamic images Io, Ia and Ip.

Figure 14:
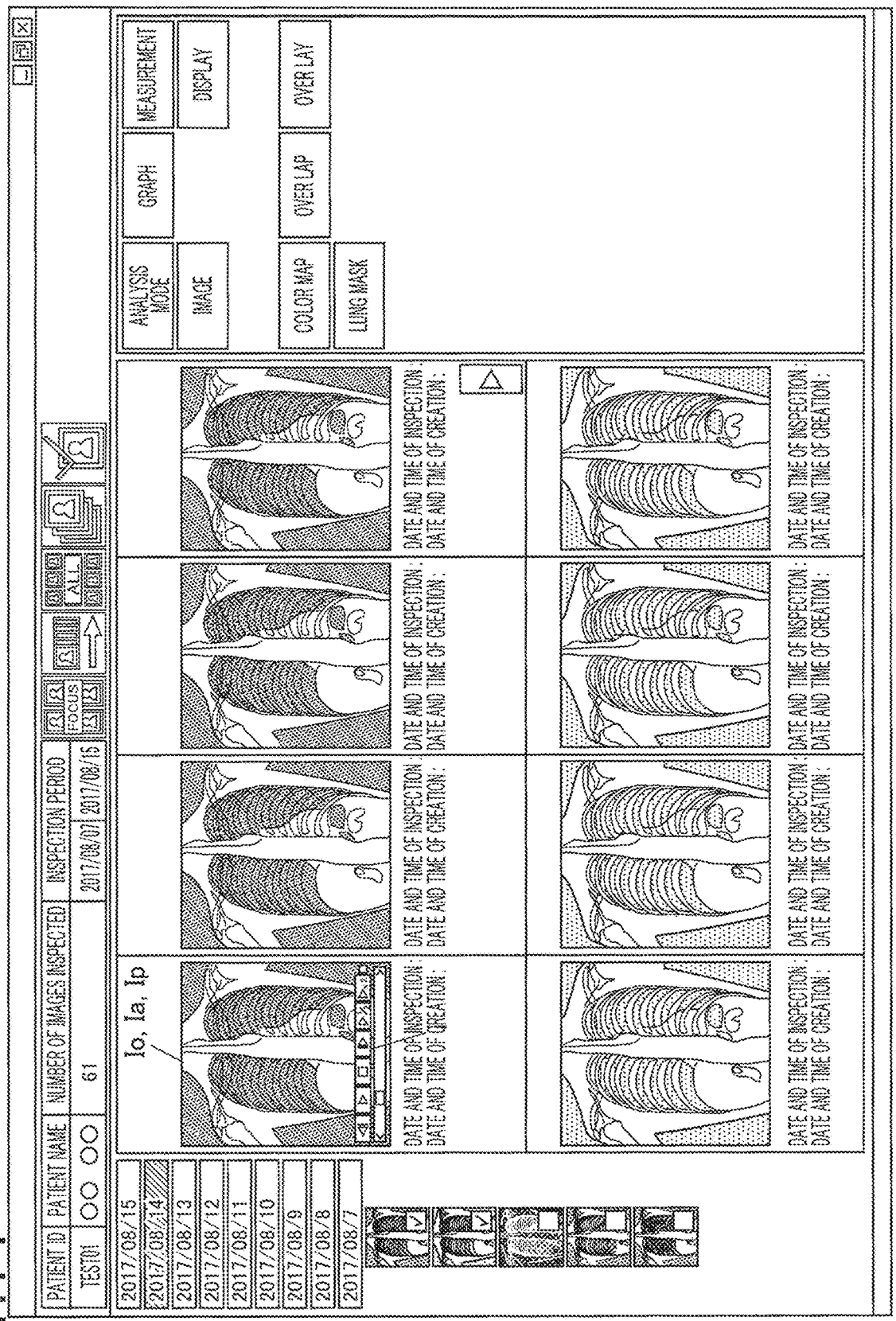
FIG. 14 shows an example of a display screen of the radiation image display apparatus in FIG. 2.

When playing back a dynamic image based on a predetermined operation (e.g., pressing of button type icons i for instructing playback or stop of a moving image as shown, for example, in FIG. 14), the controller 41 has a function of approximating a waveform of one of the graph corresponding to the analysis dynamic image Ia and the graph corresponding to the related dynamic image to a waveform of the other graph.

Figure 15A:
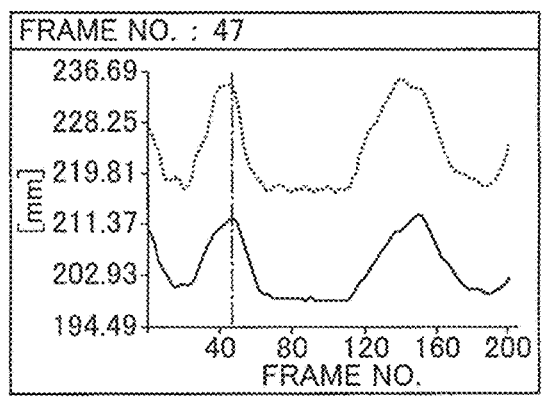
FIG. 15A, FIG. 15B, and FIG. 15C are a diagram describing waveform approximation conducted by the radiation image display apparatus in FIG. 2.
Figure 15B:
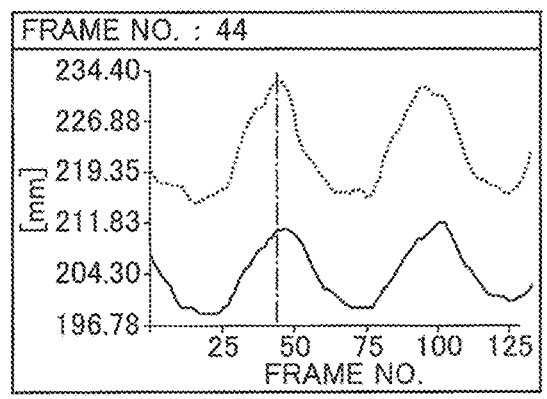
Figure 15C:
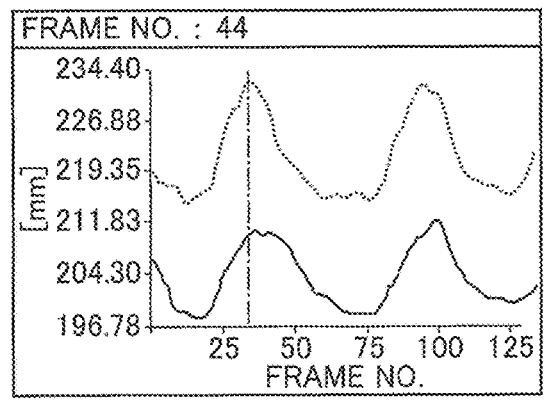

More specifically, by processing a dynamic image of an inspection B (one) corresponding to a graph shown at the right top in FIG. 15A to FIG. 15C so that the frame that becomes a local maximum (local minimum) as shown at the right bottom in FIG. 15A to FIG. 15C is shifted to the front (back), the graph is thereby approximated to a waveform of a graph of an inspection A (the other) shown at the left in FIG. 15A to FIG. 15C.

In a breathing-related dynamic image, the dynamic image does not always have the same breathing phase as that of the image captured in the past, and so time and effort are necessary for comparison and confirmation of images, whereas having such a function can save time and effort.

Furthermore, when playing back the analysis dynamic image Ia or the related dynamic image, the controller 41 has a function of partially playing back frames starting from a frame in which image capturing is performed when a distance from the pulmonary apex to the diaphragm is a maximum to a frame in which image capturing is performed when the distance is a minimum or from a frame in which image capturing is performed when the distance from the pulmonary apex to the diaphragm is a minimum to a frame in which image capturing is performed when the distance is a maximum.

Figure 16A:
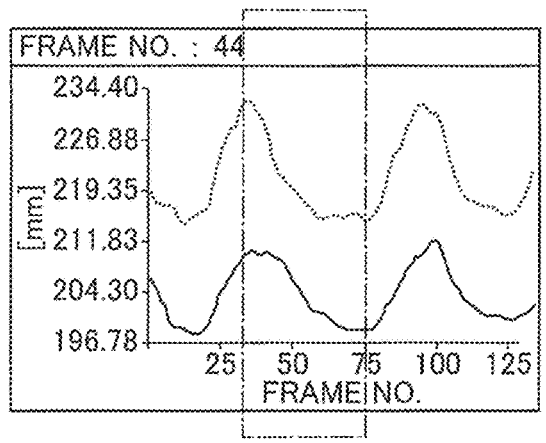
FIG. 16A, FIG. 16B and FIG. 16C are diagrams illustrating a playback range of a dynamic image.
Figure 16B:
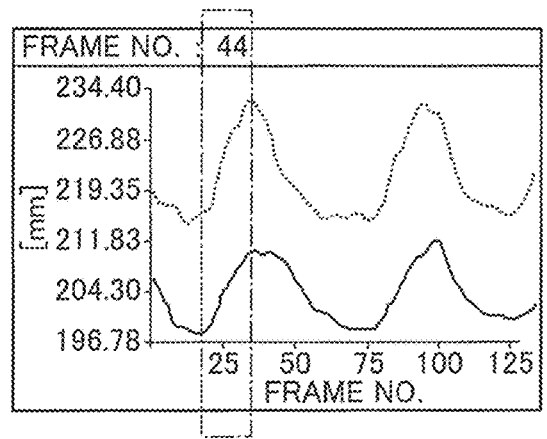

More specifically, the controller 41 plays back a range of the graph sinking to the right as shown in FIG. 16A or a range of the graph rising to the right as shown in FIG. 16B.

Figure 16C:
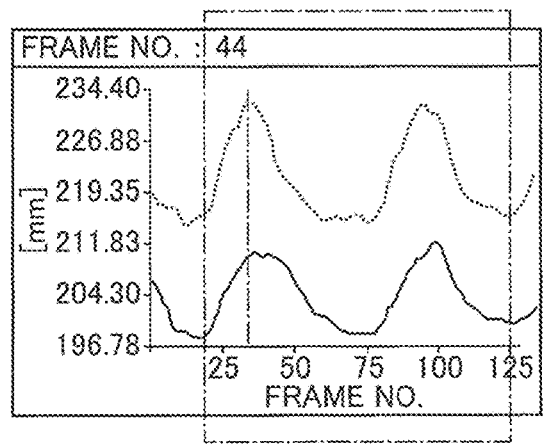

Note that the controller 41 may also play back frames starting from a frame in which an image is captured when the distance from the pulmonary apex to the diaphragm is a maximum to a frame in which an image is captured at the next and subsequent times when the distance is a maximum or from a frame in which an image is captured when the distance from the pulmonary apex to the diaphragm is a minimum to a frame in which an image is captured at the next and subsequent times (after two times in FIG. 16C) when the distance is a minimum as shown in FIG. 16C.

Furthermore, the controller 41 has a function of playing back the analysis dynamic image Ia and the related dynamic image simultaneously.

Furthermore, the controller 41 has a function of changing playback speeds of the analysis dynamic image Ia and the related dynamic image.

Figure 17:
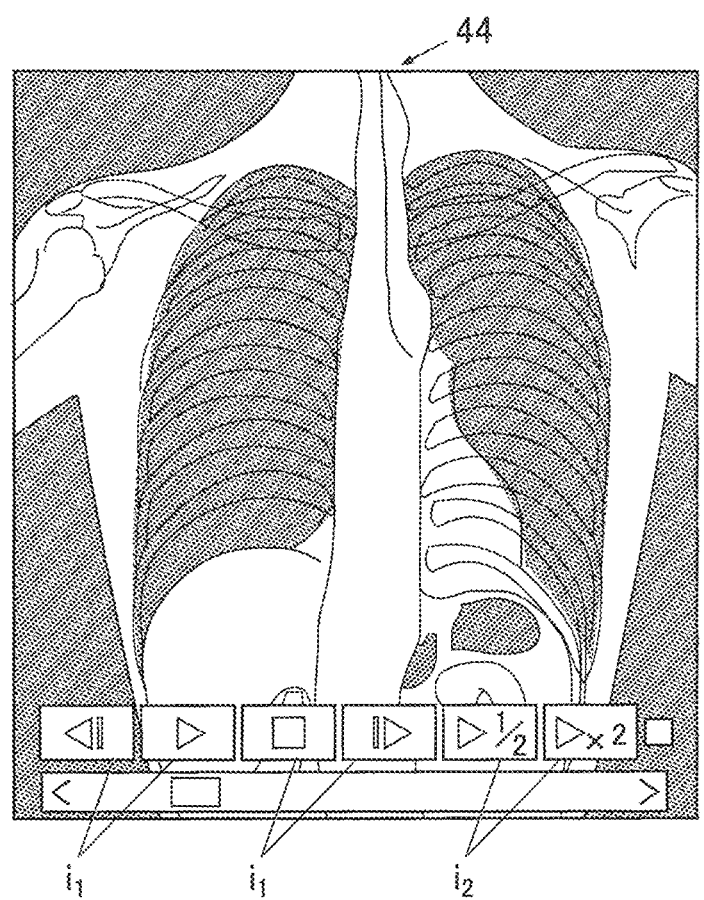
FIG. 17 is a diagram illustrating part of a display screen of the radiation image display apparatus in FIG. 2.

More specifically, as shown in FIG. 17, for example, icons i2 for indicating ½-speed playback and double-speed playback are added to the button type icons it for indicating playback or stoppage of a moving image. When this icon i2 is touched or clicked, dynamic images are played back at a speed ½ or twice the normal speed.

Having such a function makes it possible to slowly play back a range of a dynamic image to be preferably observed attentively or to quickly finish playback of a range of a dynamic image which is not so important.

As described above, the display apparatus 4 provided for the imaging system 100 according to the present embodiment is provided with the displayer 44 and the controller 41 that acquires image data of a dynamic image constituted of a plurality of frame images, image data of an analysis dynamic image Ia obtained by applying predetermined image processing to image data of the dynamic image and image data of a related dynamic image Ip related to the dynamic image or the analysis dynamic image Ia respectively and causes the displayer 44 to display the related dynamic image Ip together with the original dynamic image Io and the analysis dynamic image Ia.

Having such a function allows the displayer 44 to display the original dynamic image Io, the analysis dynamic image Ia and the related dynamic image simultaneously, thereby making it relatively easy to compare a comparison source dynamic image with comparison target dynamic images Io, Ia and Ip.

Although the present invention has been described specifically based on the embodiment so far, it goes without saying that the present invention is not limited to the above embodiment and can be changed as appropriate without departing from the spirit and scope of range.

[Associated Techniques]

Next, associated techniques applicable to a radiation imaging system in general having an image analysis function and an image display function including the radiation imaging system 100 according to the above embodiment will be described.

[Generation of Analysis Dynamic Image]

Radiation imaging systems involve a problem that performing various kinds of image processing based on operation of the operating part 45 requires time and effort.

Figure 18:
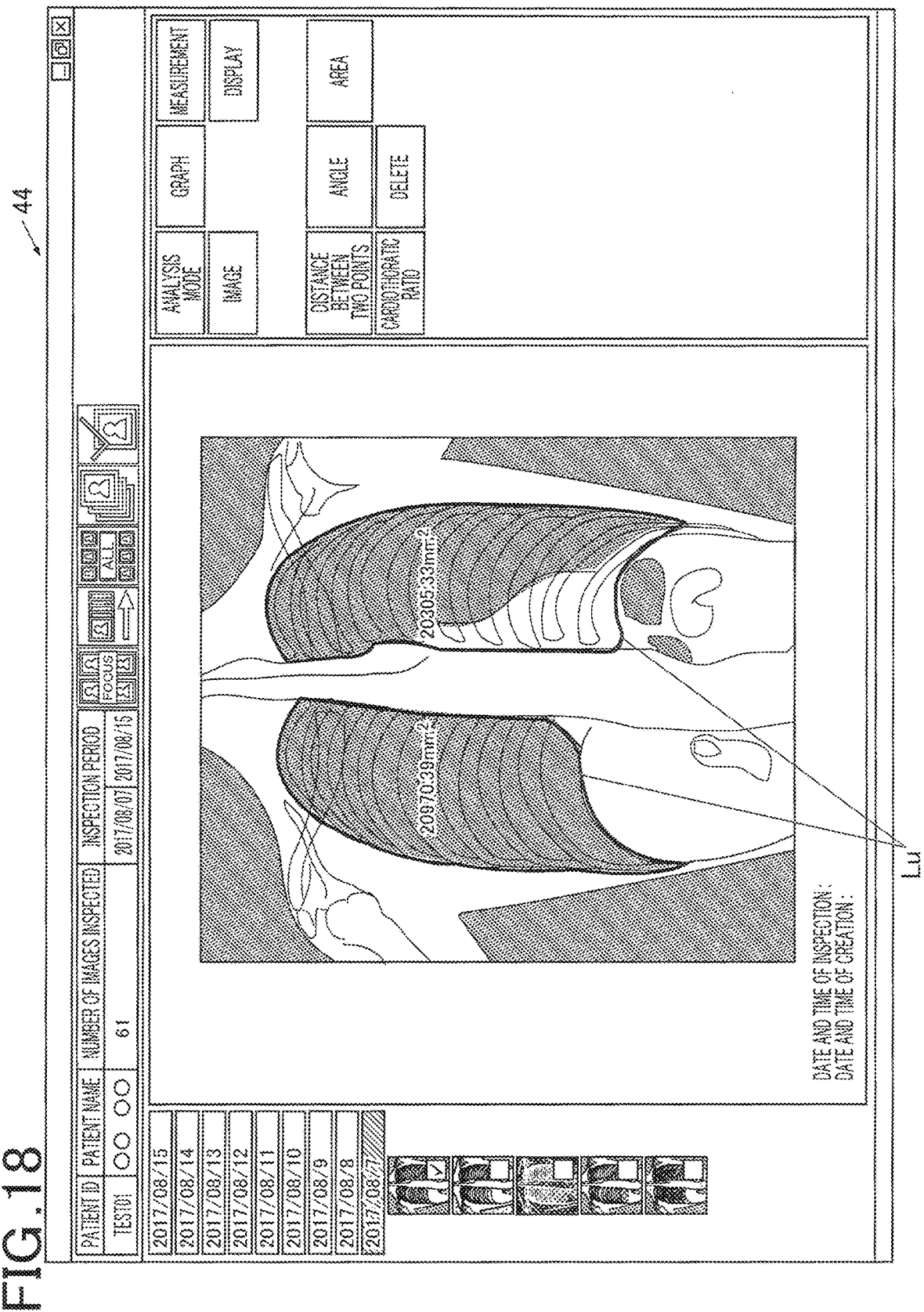
FIG. 18 shows an example of a display screen of a radiation image display apparatus according to an associated technique.

In view of such a problem, a necessary dynamic analysis or measurement of an internal area of the lung field (area of the region shown by a reference character Lu in FIG. 18) based on predetermined conditions (e.g., image capturing conditions, disease) when image data of a dynamic image is acquired may be automatically executed and the analysis and measurement results may be displayed on the displayer 44.

By so doing, it is possible to save time and effort required to select necessity or unnecessity of a dynamic analysis and area calculations executed by the user.

Furthermore, setting conditions for the dynamic analysis and area calculations may avoid unnecessary dynamic analyses.

Furthermore, the radiation imaging systems involve a problem that even when a dynamic analysis is preferred to be performed urgently for a high priority subject such as an emergency patient, if an analysis of a dynamic image of another subject is already in progress or there is a queue of dynamic analyses to be executed, it is impossible to proceed to the next dynamic analysis.

In view of such a problem, the processing order may be changed according to priority or parallel processing may be allowed to be executed.

By so doing, it is possible to perform a dynamic analysis starting from inspection with high priority.

Parallel processing allows the analysis to be finished earlier.

Diagnoses using radiation imaging systems also involve a problem that when parameters used for a new dynamic analysis are different from parameters used for past dynamic analyses, it is difficult to compare an analysis dynamic image Ia obtained by the new dynamic analysis with an analysis dynamic image Ia obtained by the past dynamic analyses.

In view of such a problem, the parameters of the past images may also be used for the new dynamic analysis.

By so doing, it is possible to facilitate comparison between the analysis dynamic image Ia obtained by the new dynamic analysis and the analysis dynamic images Ia obtained by the past dynamic analyses.

In the radiation imaging system, parameters used for past dynamic analyses are not always stored in the analysis apparatus used for a new dynamic analysis. If parameters used in the past are stored in another apparatus, the problem is that the user cannot find the parameters used in the past, which prevents the past parameters from being used for a new dynamic analysis.

Figure 19:
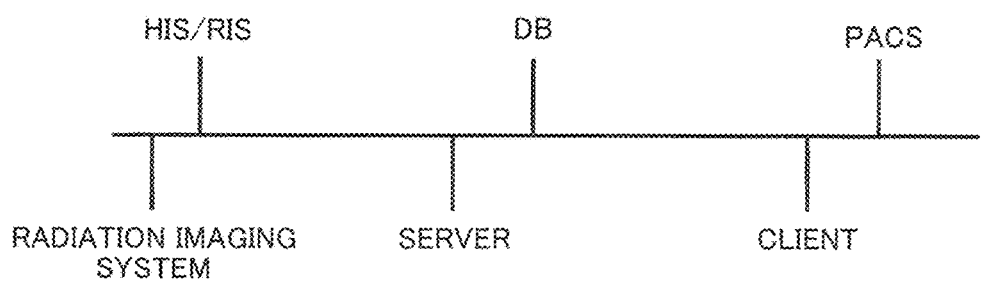
FIG. 19 is a diagram illustrating connection between a radiation imaging system according to the associated technique and another apparatus.

In view of such a problem, as shown, for example, in FIG. 19, the radiation imaging system may be connected to a server, PACS, database, HIS, RIS or the like and parameters used for past dynamic analyses may be saved in one of these apparatuses.

By so doing, it is possible to share past parameters among the respective apparatuses connected to these apparatuses and solve the problem that past parameters cannot be used.

In the radiation imaging system, when an analysis of a dynamic image of another subject is already in progress or there is a queue of dynamic analyses to be executed, there is a problem that it is unknown how many new analysis dynamic images Ia can be confirmed.

Figure 20:
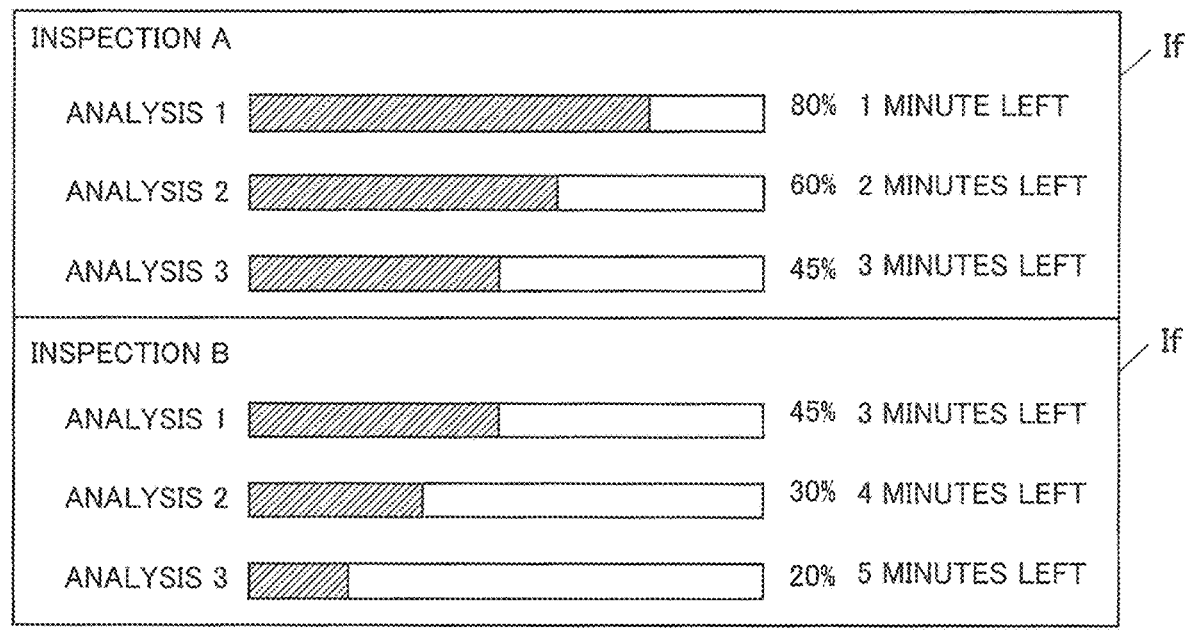
FIG. 20 is a diagram illustrating part of a display screen of the radiation image display apparatus according to the associated technique.
Figure 23:
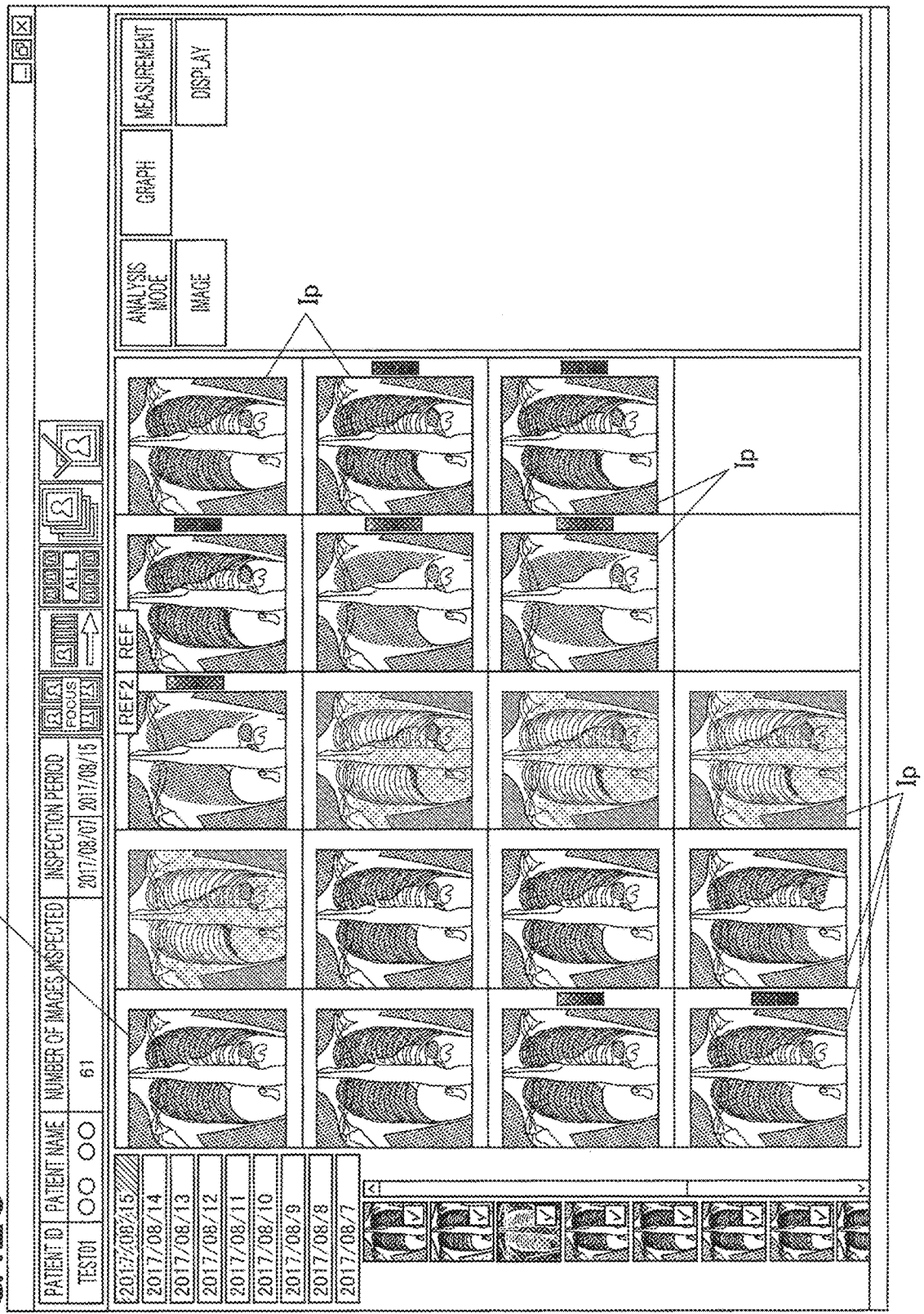
FIG. 23 shows an example of a display screen of the radiation image display apparatus according to the associated technique.

In view of such a problem, as shown, for example, in FIG. 20, information If such as contents and the number of dynamic analysis to be executed, progress of a dynamic analysis (at least one of graph and numerical value) and a remaining time until the end of a dynamic analysis or the like may be displayed.

Figure 21:
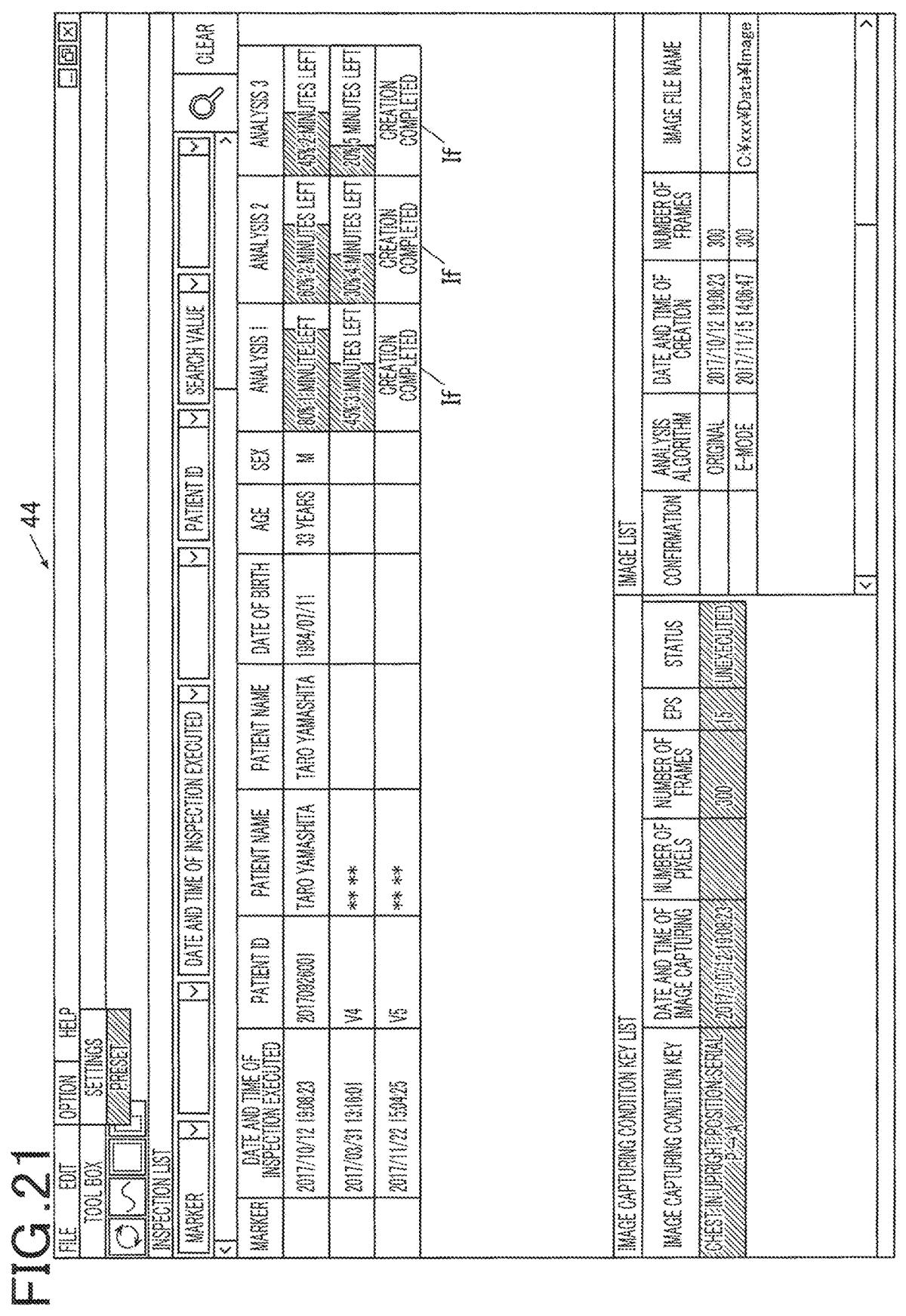

Note that such information If may also be displayed in a list of inspections as shown, for example, in FIG. 21.

By so doing, it is possible to make an estimate as to when a new analysis dynamic image Ia can be confirmed and it is thereby easier to schedule an overall inspection.

[Image Display/Image Confirmation]

In the radiation imaging system, it is often the case that there are a plurality of types of related dynamic images in the same inspection and there may be cases where the displayer does not have an enough space to display all the related dynamic images. In that case, it is necessary to confirm one by one what related dynamic images exist among related dynamic images which are not displayed, which takes time and effort.

In view of such a problem, the number of frames to be displayed at a time may be changed depending on the number of types of related dynamic images.

Figure 22:
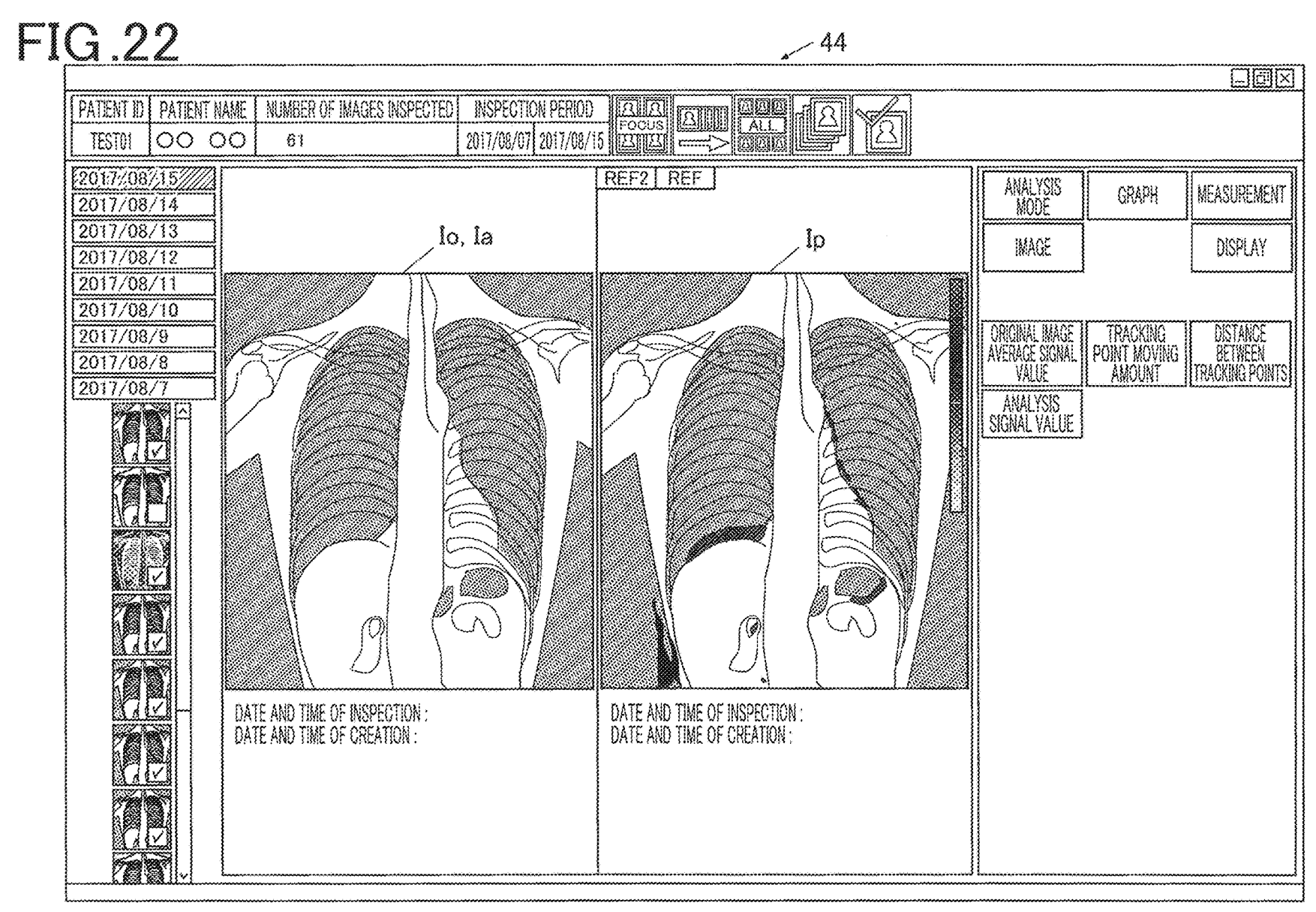

More specifically, when the number of types of related dynamic images Ip is small, the number of frames may be reduced as shown, for example, in FIG. 22 and each related dynamic image is displayed in an enlarged size, or when the number of types is large, the number of frames is increased and each related dynamic image is displayed in a small size.

By so doing, even when there are many related dynamic images, it is possible to easily confirm or grasp the related dynamic images.

Furthermore, in the radiation imaging system, if there are a plurality of original dynamic images Io in the same inspection, there is a problem that when the original dynamic image Io and the analysis dynamic image Ia are displayed together, it becomes uncertain to which original dynamic image Io, the analysis dynamic image Ia corresponds.

Figure 24:
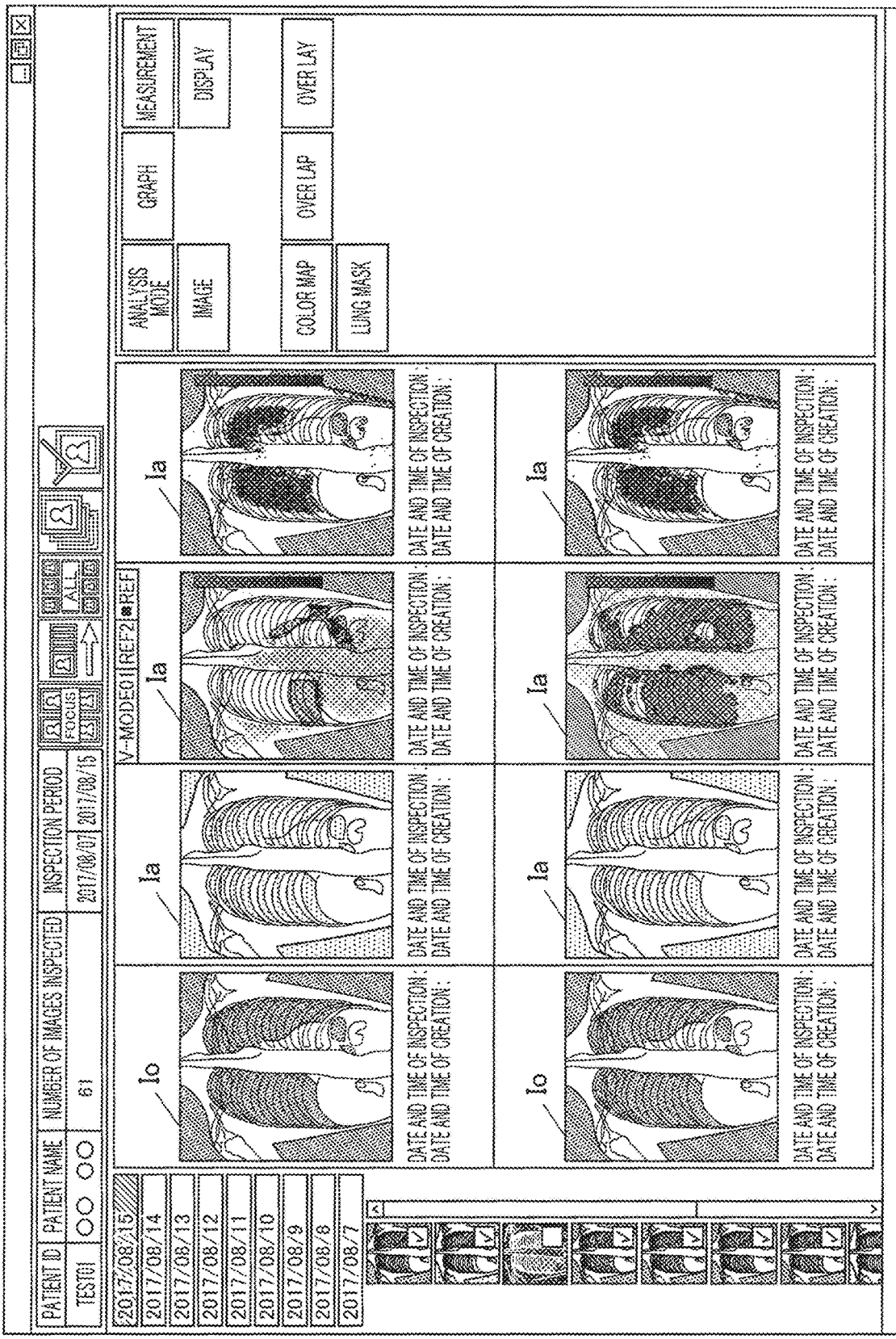
FIG. 24 shows an example of a display screen of the radiation image display apparatus according to the associated technique.
Figure 25:
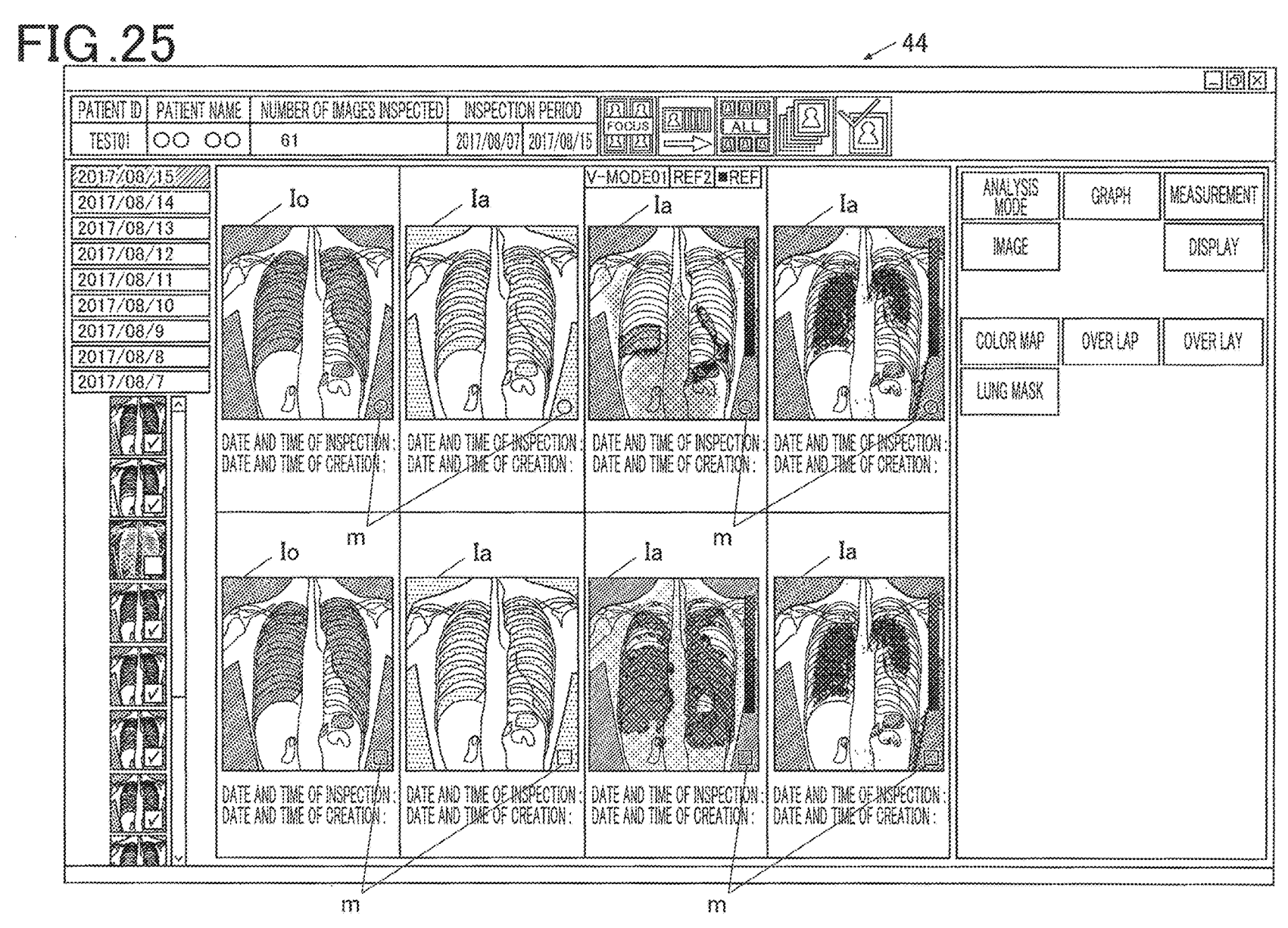

In view of such a problem, as shown, for example, in FIG. 24, the dynamic image Io and the analysis dynamic image Ia may be arranged in one line (here, arranged laterally in a row) or as shown in FIG. 25, the same mark m may be added to the original dynamic image Io and the corresponding analysis dynamic image Ia.

By so doing, it is easier to grasp the original dynamic image Io and the corresponding analysis dynamic image Ia.

In the radiation imaging system, when, for example, an attempt is made to carry out drag-and-drop using a mouse to add a dynamic image to be displayed, it is necessary to perform an operation of increasing the number of frames, which takes time and effort.

In view of such a problem, a list of thumbnail images for the acquired analysis dynamic images Ia and related dynamic images may be displayed and a predetermined selection operation may be performed on a thumbnail image for a dynamic image to be displayed to thereby allow displaying/non-displaying of dynamic images to be switched and change the number of frames to be displayed at a time depending on the number of dynamic images to be displayed (the number of selected thumbnail images) and depending on the number of images.

Figure 26:
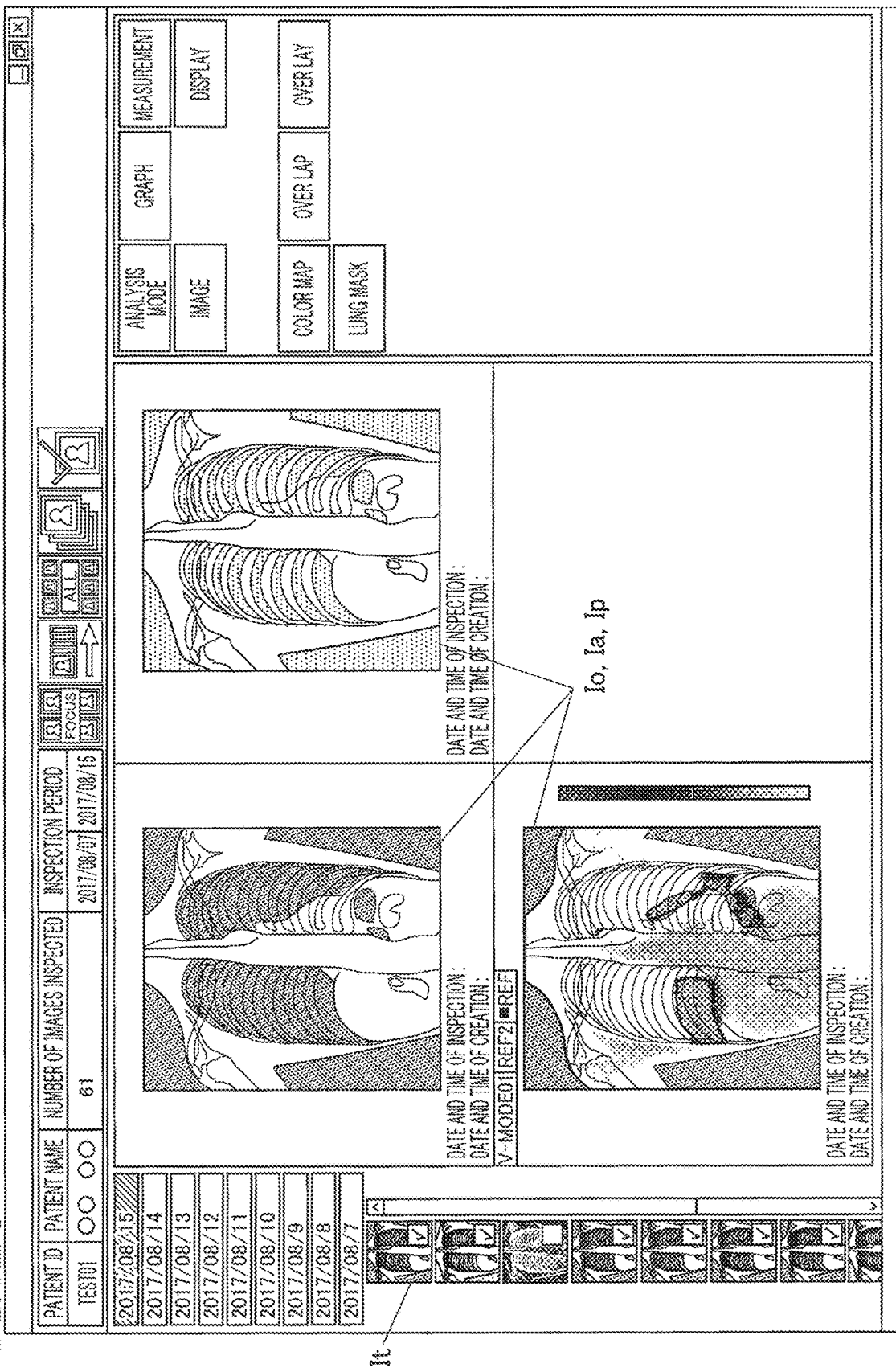
FIG. 26 shows an example of a display screen of the radiation image display apparatus according to the associated technique.

As shown in FIG. 26, examples of the method of selecting thumbnail images include checking checkboxes provided for the respective thumbnail images It and clicking on the thumbnail images It themselves.

Figure 27:
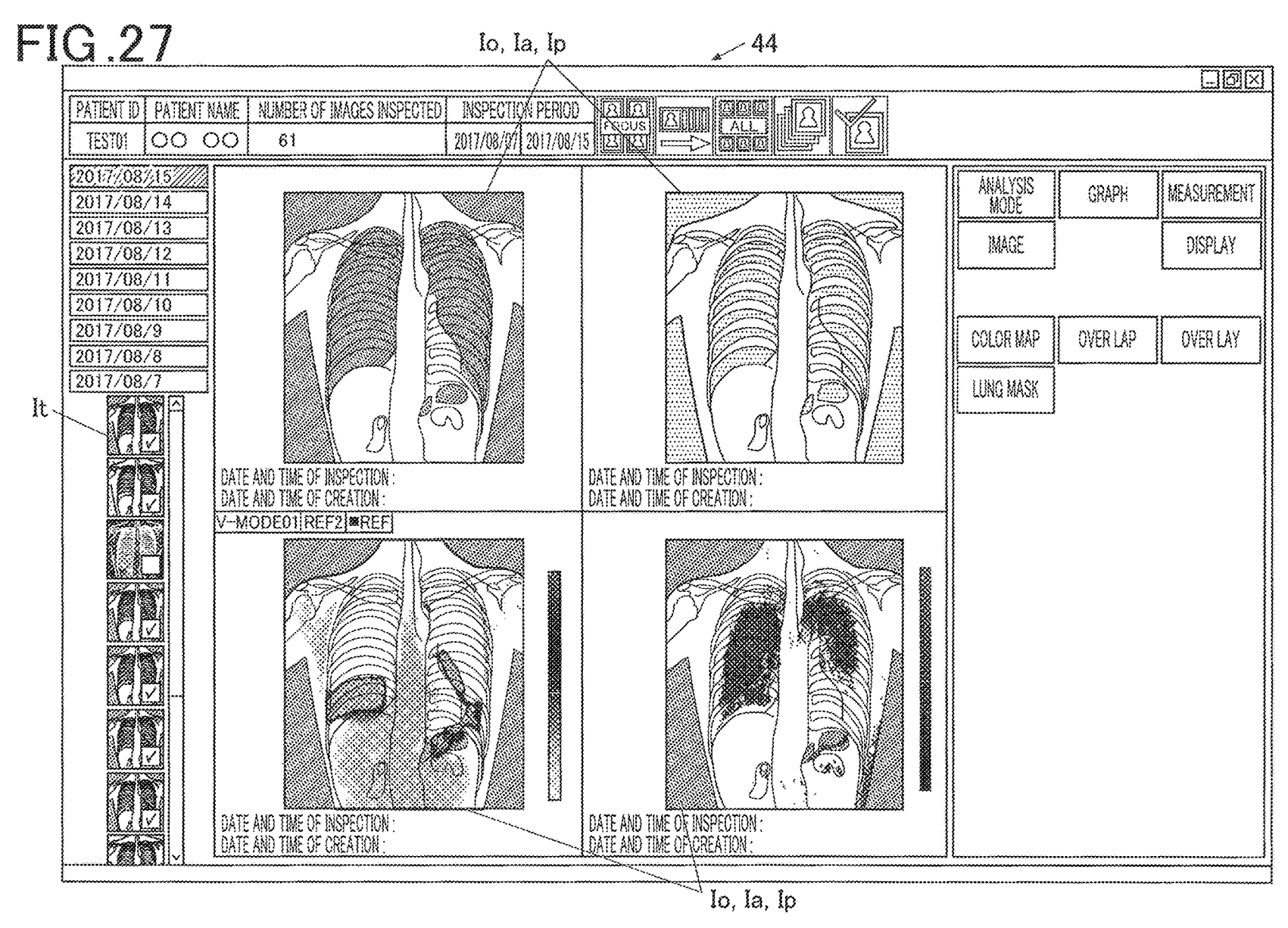

Dynamic images corresponding to the selected thumbnail images It are displayed. If the number of thumbnail images to be selected is increased, the number of dynamic images to be displayed is also increased as shown in FIG. 27.

By so doing, it is possible to add dynamic images without the need for performing operation to change the number of frames or moving the mouse.

Since displaying/non-displaying operation of dynamic images is performed in the thumbnail region, it is possible to reduce the amount of movement of the mouse.

In the radiation imaging system, when one dynamic image is displayed in a large size over a whole image display region within the displayer, if another dynamic image needs to be displayed, for example, if an attempt is made to display the other dynamic image by carrying out drag-and-drop of the corresponding thumbnail image using the mouse, the amount of movement of the mouse increases and operability deteriorates.

In view of such a problem, which dynamic image of image data of the acquired dynamic images is to be displayed (switched) may be assigned to keys of a keyboard and a mouse or the like in advance so that when a predetermined keyboard operation or mouse operation is carried out, the corresponding dynamic image is displayed.

Figure 28:
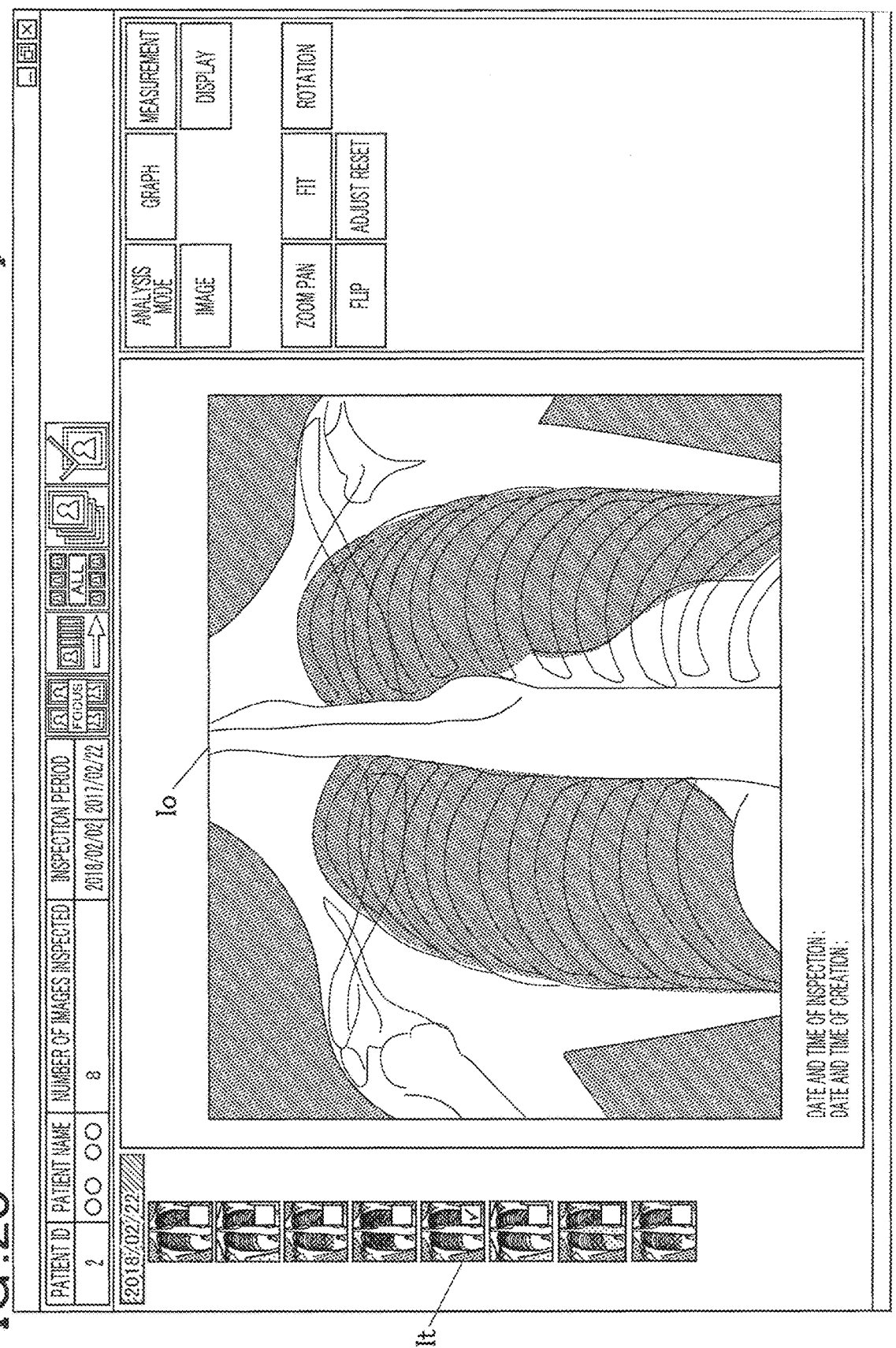
FIG. 28 shows an example of a display screen of the radiation image display apparatus according to the associated technique.
Figure 29:
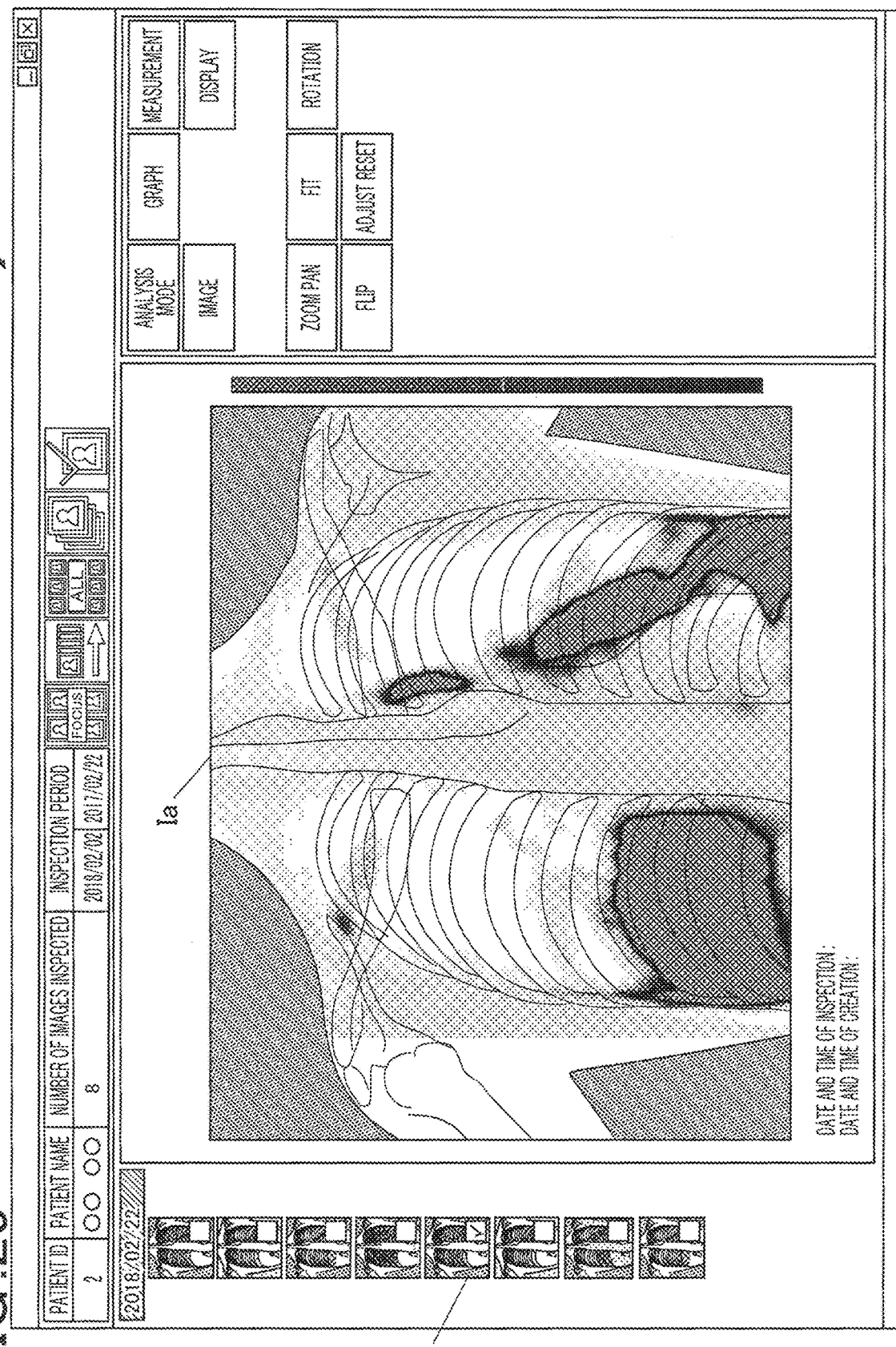
FIG. 29 shows an example of a display screen of the radiation image display apparatus according to the associated technique.

By so doing, when a specific key operation or mouse operation is carried out while a certain dynamic image (e.g., original dynamic image Io) is displayed as shown, for example, in FIG. 28, another dynamic image (e.g., analysis dynamic image Ia) as shown in, FIG. 29 is displayed, and it is thereby possible to perform changeover to a desired dynamic image without largely moving the mouse.

In the radiation imaging system, when all the thumbnail images of acquired dynamic images are arranged side by side, it is necessary to largely scroll the list of thumbnail images to reach a thumbnail image of a dynamic image to be displayed, which takes time and effort.

Figure 30:
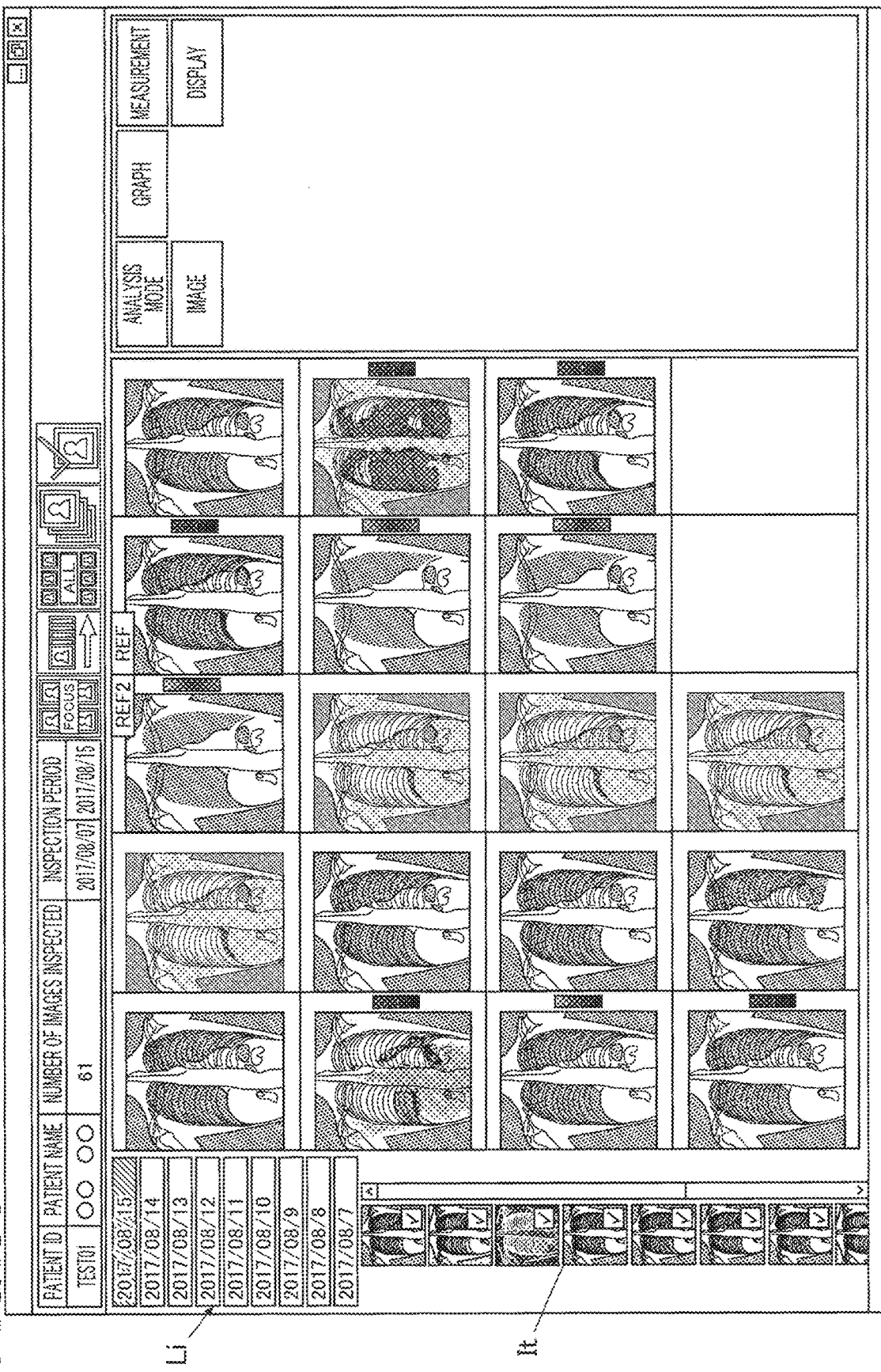
FIG. 30 shows an example of a display screen of the radiation image display apparatus according to the associated technique.

In view of such a problem, as shown, for example, in FIG. 30, a list Li of a plurality of inspections carried out for the same patient may be displayed on the displayer 44, and only thumbnail images It of dynamic images corresponding to the inspections selected from the list Li may be displayed.

By so doing, it is possible to facilitate finding of a target inspection and facilitate referencing of the corresponding thumbnail image.

The radiation imaging system involves a problem that if there are a plurality of similar types of analysis dynamic images Ia obtained by applying similar types of image processing while changing parameters, it is not possible to determine which parameter is used to process an analysis dynamic image Ia for a diagnosis.

Figure 31:
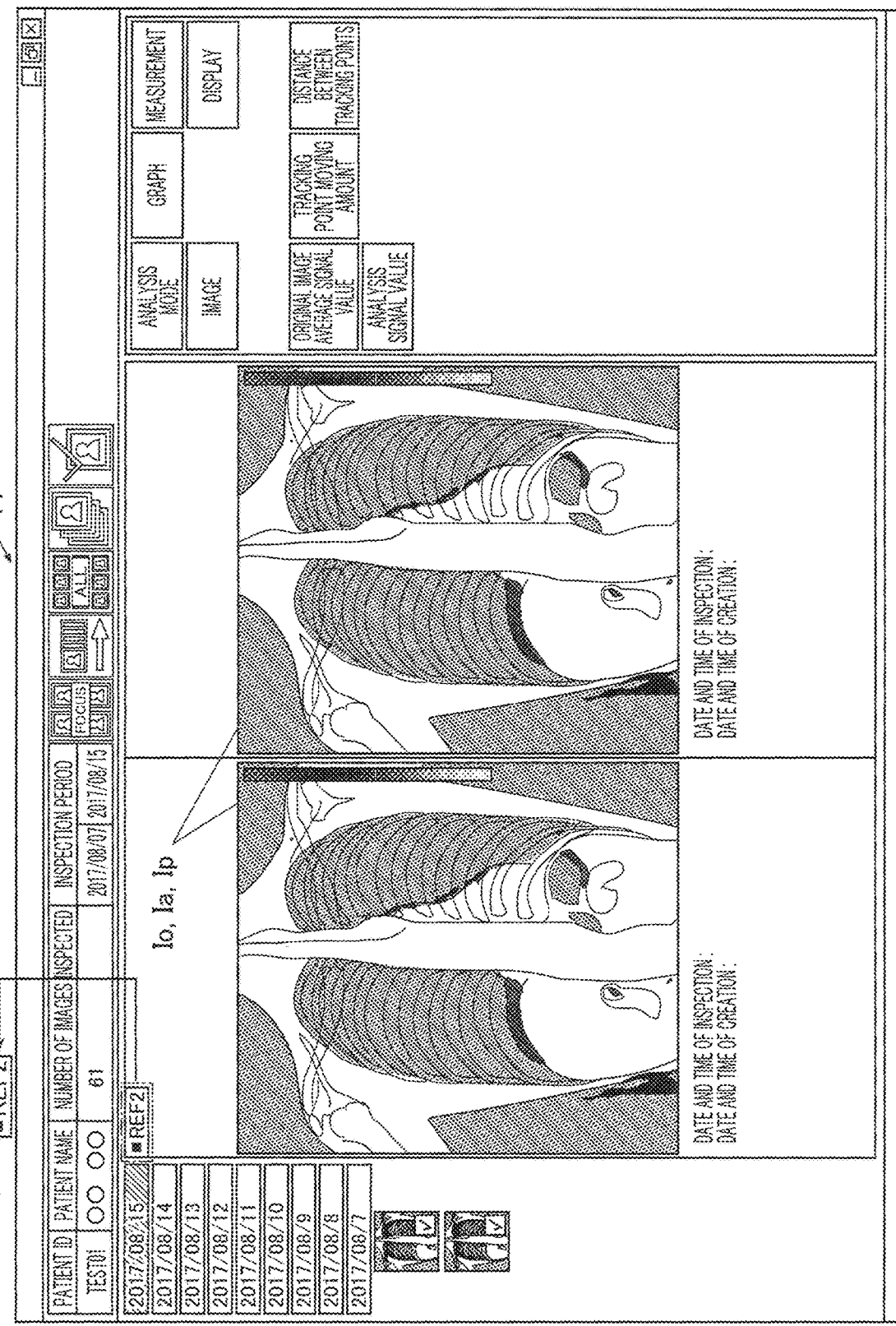
FIG. 31 shows an example of a display screen of the radiation image display apparatus according to the associated technique.

In view of such a problem, as shown, for example, in FIG. 31, a predetermined mark m may be displayed in the vicinity (e.g., tab t) of one of similar dynamic images Io, Ia and Ip with different parameters. It is assumed that the mark m can be displayed for only one of the dynamic images Io, Ia and Ip of the same inspection.

Furthermore, dynamic images Io, Ia and Ip of the same type with different parameters may be switchable between a switching display with tabs t1 and t2, and a display in parallel.

By so doing, it is possible to determine which analysis dynamic image Ia is for a diagnosis on the basis of the presence or absence of a mark.

Adopting tab switching as the display method allows only a dynamic image determined for a diagnosis to be displayed.

Furthermore, the radiation imaging system involves a problem that when there are a plurality of analysis dynamic images Ia of the same type obtained by applying image processing of the same type while changing parameters, it takes time to locate a difference in analysis results.

In view of such a problem, analysis dynamic images Ia of the same type with different parameters may be superimposed and displayed, and the level of difference between both images may be distinguished by using different colors.

By so doing, when there are a plurality of analysis dynamic images Ia of the same type with different parameters, it is possible to easily grasp the differences.

[Playback of Dynamic Image]

Furthermore, the radiation imaging system involves a problem that when an analysis dynamic image Ia and a related dynamic image are compared while both images are being played back, it is difficult to compare the images when breathing timings do not match.

In view of such a problem, playback timings of both images may be matched based on the respective frame images of the analysis dynamic image Ia and the related dynamic image.

More specifically, state changes of movable regions of the respective dynamic images (e.g., ascending/descending motion of the diaphragm) may be examined, and frame images corresponding to timing at which the states of the movable regions of the respective dynamic images are substantially matched (e.g., when the diaphragm ascends (descends) to the highest (lowest) position) and the frame images may be played back.

By so doing, it is possible to compare the analysis dynamic image Ia and the related dynamic image in a matched breathing state without the need to use a graph.

In the radiation imaging system, during playback of a dynamic image, if another image needs to be subjected to image processing (e.g., gradation processing, image enlargement/contraction), the playback of the dynamic image needs to be suspended, which takes time and effort.

In view of such a problem, it may be possible to apply specific image processing to image data of the dynamic image under playback.

By so doing, it is possible to apply other image processing without suspending the playback of the dynamic image.

[Past Image Display]

In the radiation imaging system, even when the user finds points in a displayed graph the user worries about and wants to confirm the corresponding frame image, the user has to find the frame image while confirming frame images one by one starting from those seemingly close to the target image, which takes time and effort.

In view of such a problem, it may be possible to switch between frame images through operation on a graph.

Figure 33:
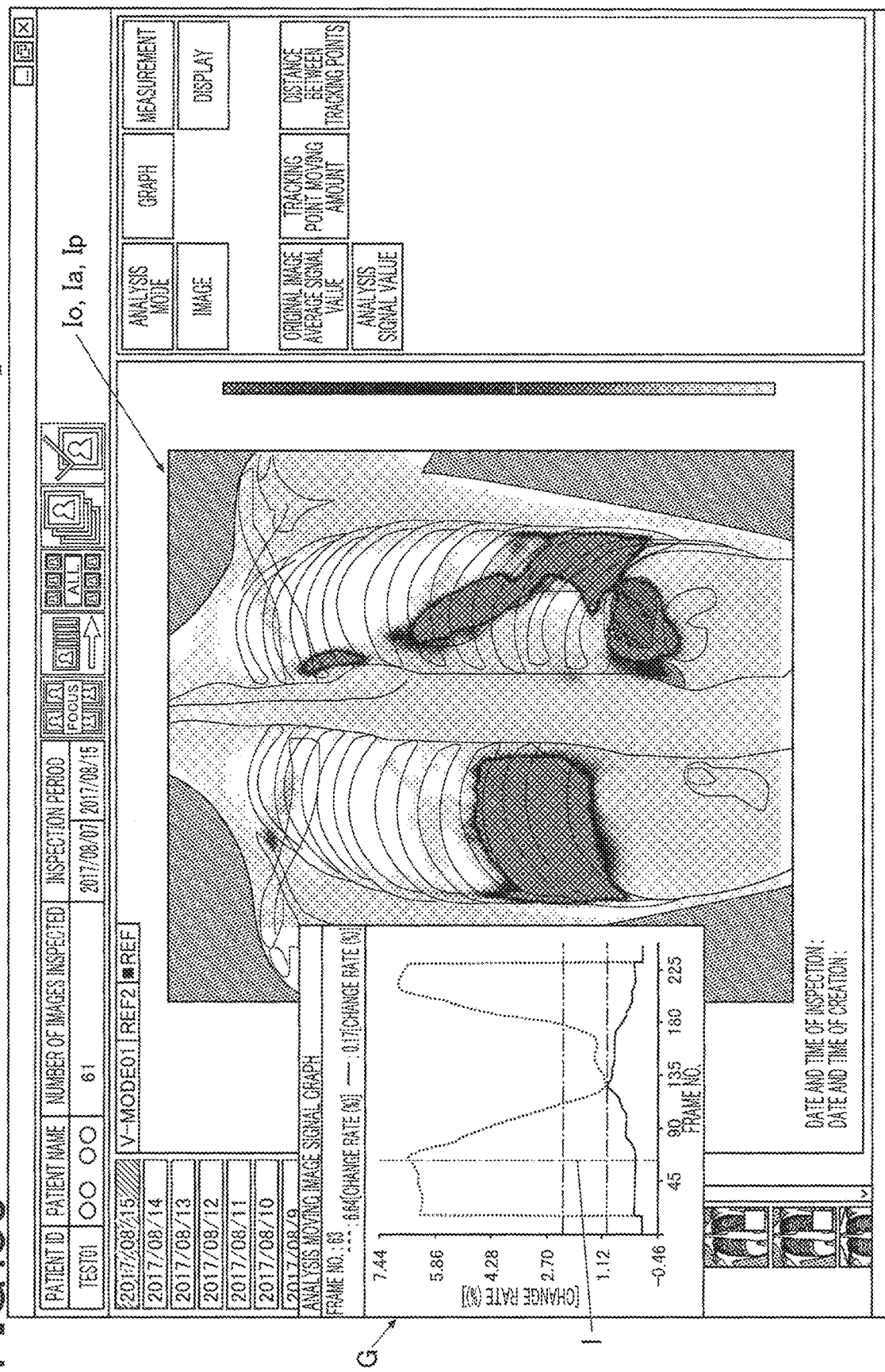
FIG. 33 shows an example of a display screen of the radiation image display apparatus according to the associated technique.

More specifically, as shown in FIG. 33, a graph G, dynamic images Io, Ia and Ip are displayed respectively. In the graph G, it may be possible to display a longitudinal line 1 parallel to the vertical axis which can be moved through, for example, a drag operation. Furthermore, a frame image with a number at a point at which the longitudinal line 1 crosses the horizontal axis is displayed.

Figure 34:
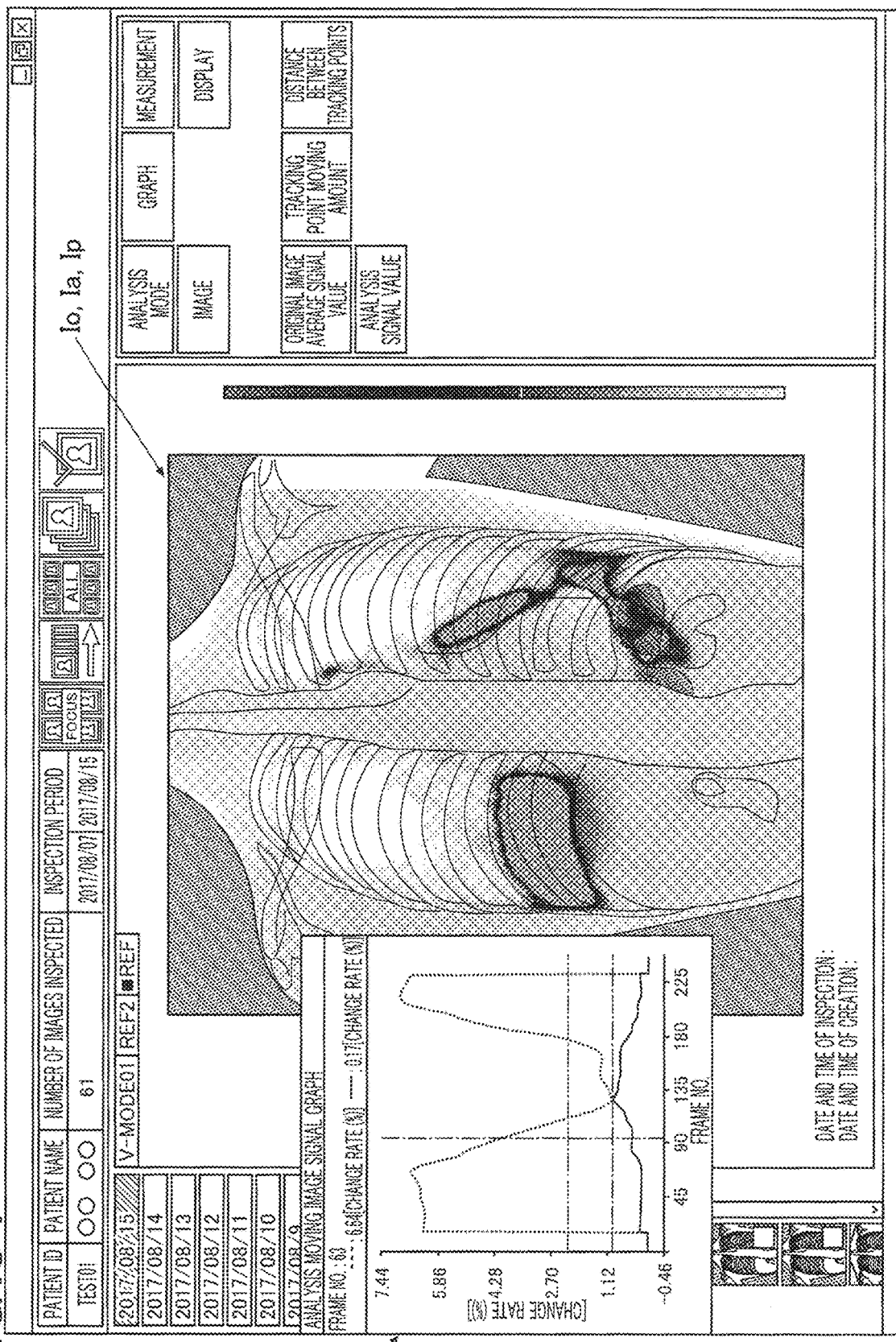
FIG. 34 shows an example of a display screen of the radiation image display apparatus according to the associated technique.

By so doing, by only moving the longitudinal line 1 to a point in the graph G the user worries about, it is possible to instantaneously display the frame image corresponding to the movement destination as shown, for example, in FIG. 34.

Furthermore, in the radiation imaging system, when inspections are repeated, a display position of a dynamic image displayed on the displayer 44 is shifted, and so when a graph is displayed at a position at which the graph was displayed at the time of a previous diagnosis, the image may be shielded. Moreover, when the graph displayed at the time of a past diagnosis is displayed together, the past graph is displayed on the actual graph, and so it is necessary to move the graph.

Figure 35:
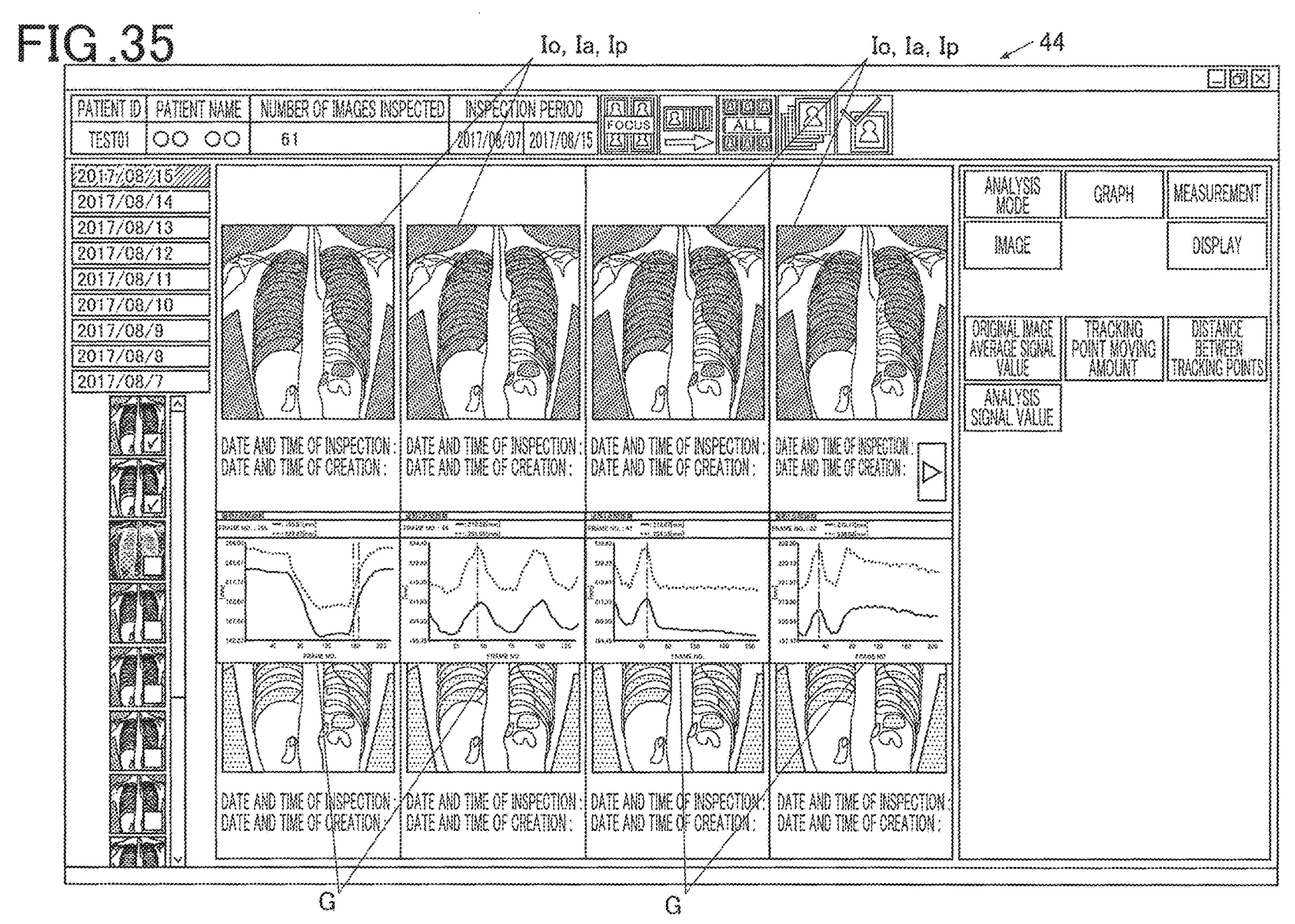

In view of such a problem, the graphs G corresponding to the dynamic images Io, Ia and Ip may be displayed adjacent to the corresponding dynamic images Io, Ia and Ip as shown in FIG. 35 (for example, below).

Figure 36:
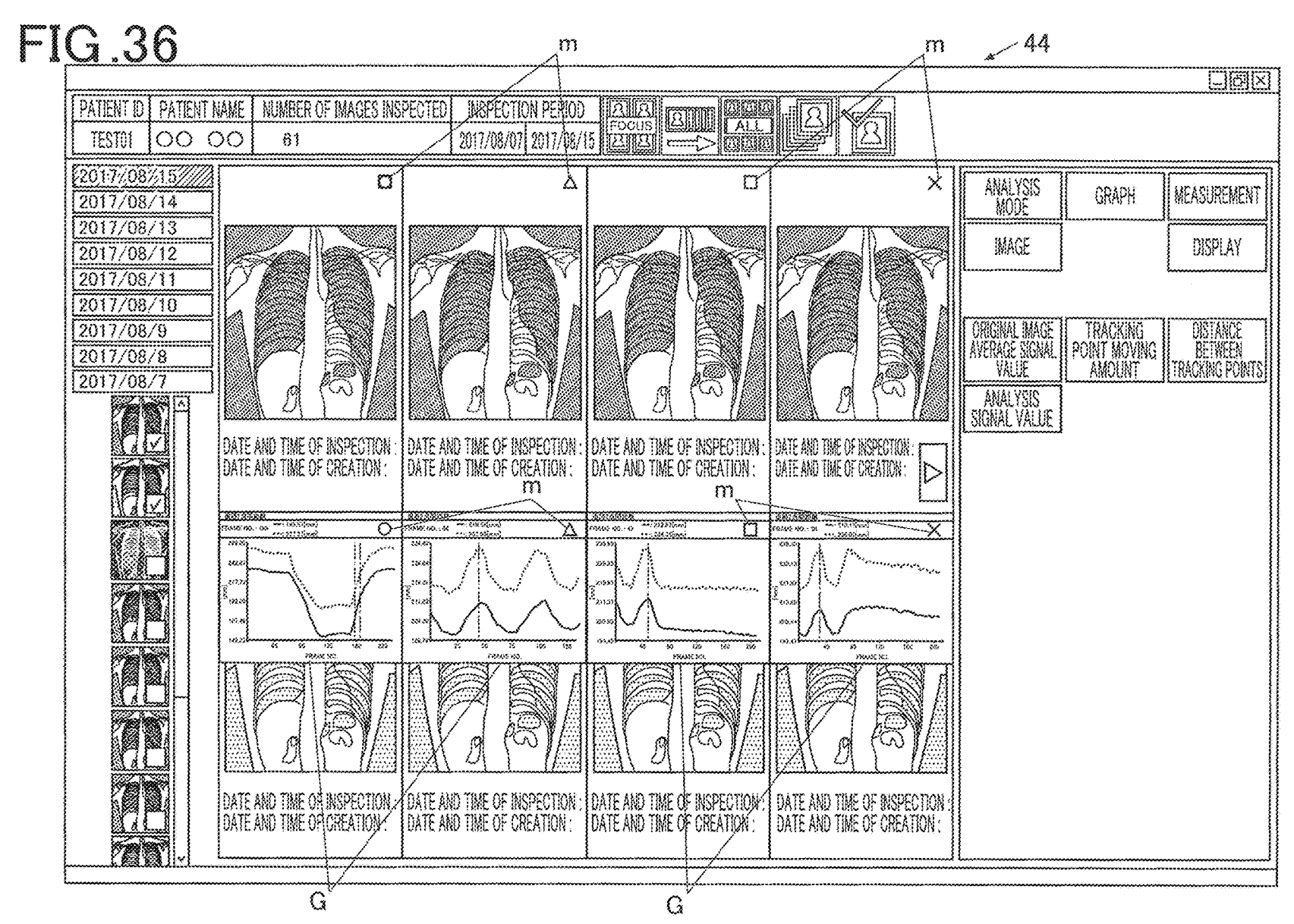

Note that as shown in FIG. 36, marks m and colors indicating association between the dynamic images Io, Ia and Ip and the graph G, and lines indicating links may be displayed.

By so doing, it is possible to arrange the dynamic images Io, Ia and Ip including the related dynamic images and the graphs G from the time of initial display and confirm the images.

Furthermore, it is also possible to perform comparison between the graphs G.

Furthermore, in the radiation imaging system, it is not possible to visually recognize regions corresponding to maximum, minimum and average signal values in an imaging target region. That is, there is a problem that signal maps in dynamic images are unknown.

Figure 37:
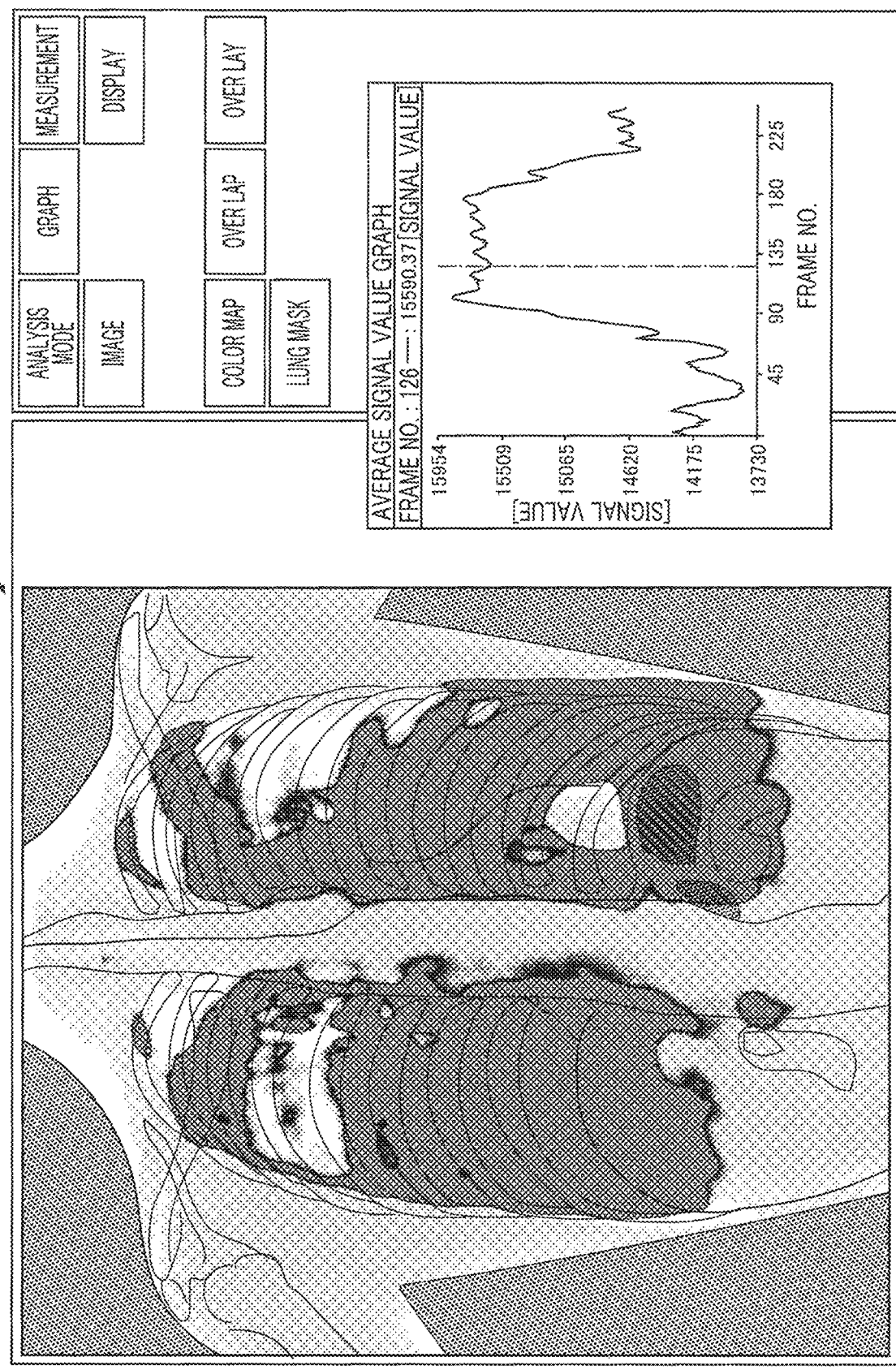
FIG. 37 shows an example of a display screen of the radiation image display apparatus according to the associated technique.

In view of such a problem, as shown, for example, in FIG. 37, when maximum, minimum and average signal values or a predetermined range are specified in a signal value graph, pixels corresponding to the specified signal value may be displayed in a specific color in the frame image displayed.

By so doing, it is possible to visually recognize the region corresponding to the maximum, minimum and average signal values in the imaging target region.

Furthermore, it is possible to grasp a signal map in the dynamic image.

[Graph Confirmation]

The radiation imaging system further involves a problem that it takes time and effort to change parameter values on a setting screen.

In view of such a problem, it may be possible to change parameter values on a graph. By so doing, parameter values can be changed easily.

In a diagnosis using the radiation imaging system, there is a problem that it is not possible to visually recognize a distance that a predetermined tracking point moves between specified frames.

Figure 38:
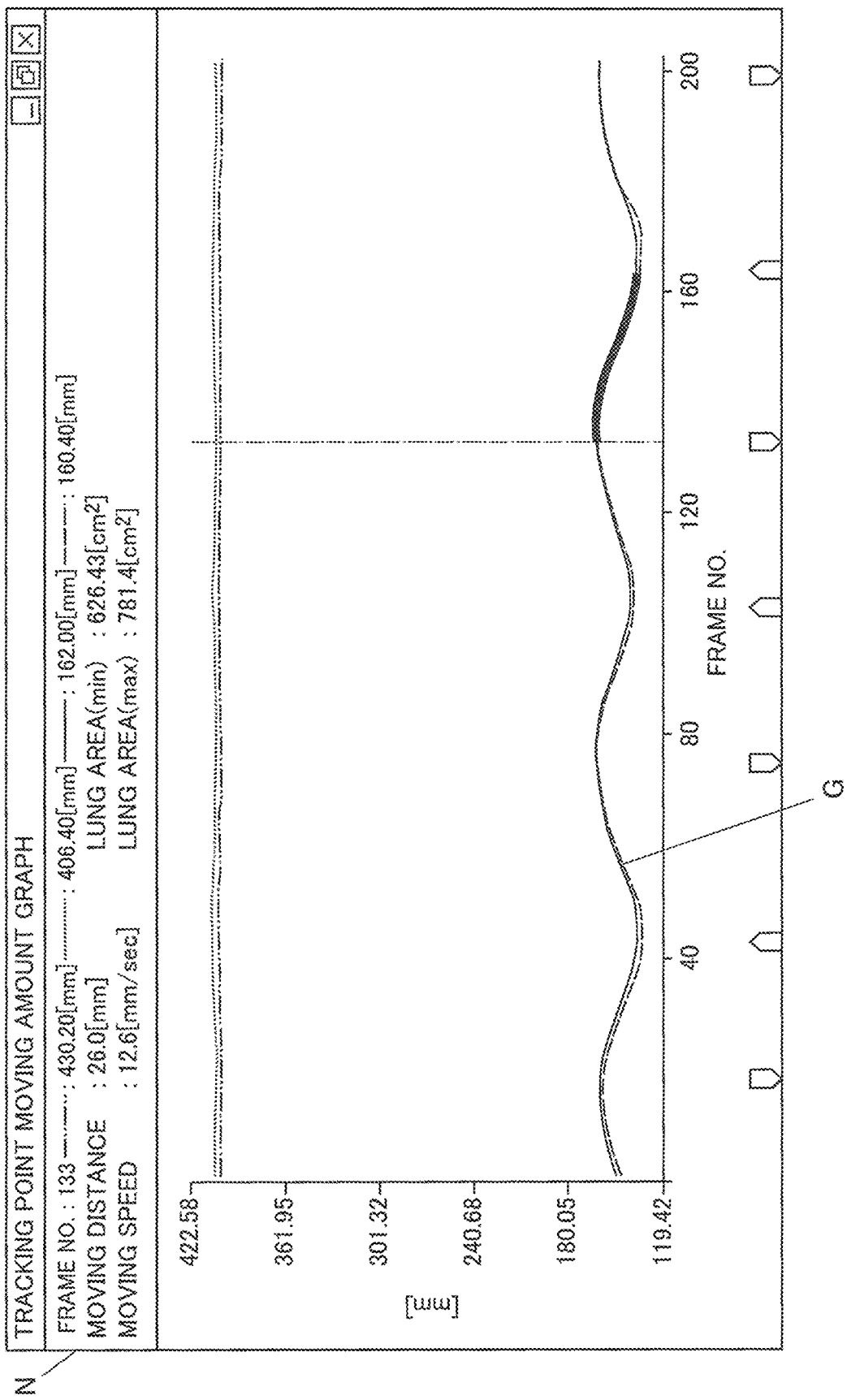
FIG. 38 shows an example of a display screen of the radiation image display apparatus according to the associated technique.

In view of such a problem, as shown, for example, in FIG. 38, numerical values N such as a time and distance that a predetermined tracking point moves between specified frames and acceleration may be displayed on the graph G.

Figure 39:
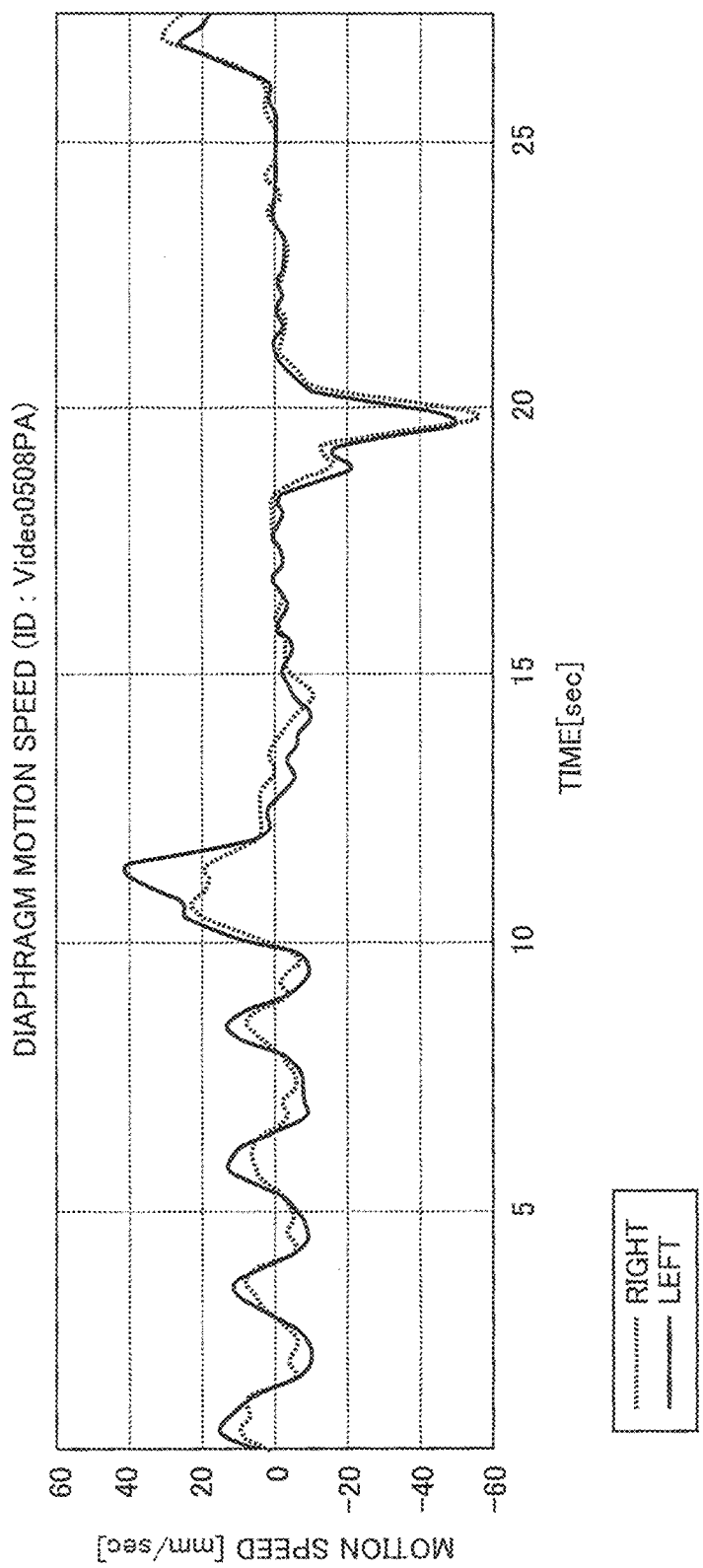
FIG. 39 is a diagram illustrating part of a display screen of the radiation image display apparatus according to the associated technique.

Furthermore, it may be possible to display a motion speed as shown, for example, in FIG. 39 in the form of a graph or the like.

By so doing, it is possible to grasp detailed analysis results.

Furthermore, the radiation imaging system involves a problem that it is difficult to visually recognize a difference between a certain dynamic image and a past dynamic image. More specifically, there is a problem that it is difficult to grasp the degree of improvement in symptoms in comparison with a past inspection.

Figure 40:
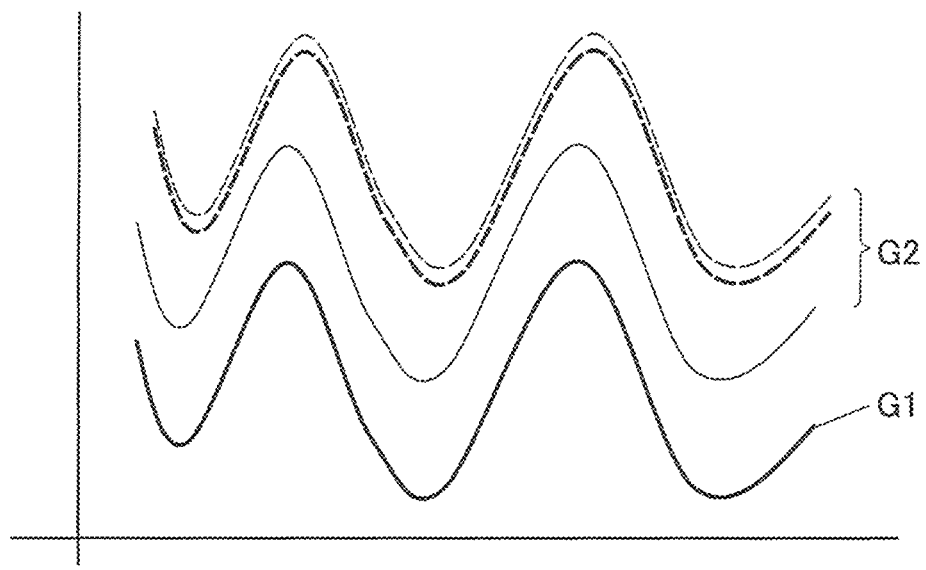
FIG. 40 is a diagram describing waveform approximation conducted by the radiation image display apparatus according to the associated technique.

In view of such a problem, as shown, for example, in FIG. 40, by causing a waveform (broken line) of a graph G2 of a related dynamic image to be approximated to a waveform (solid line) of a graph G1 of an analysis dynamic image, a difference from the past dynamic image may be displayed.

By so doing, it is possible to visually recognize a difference between a certain dynamic image and a past dynamic image.

The radiation imaging system involves a problem that it is not possible to grasp various kinds of information using a graph of a dynamic image alone.

Figure 41A:
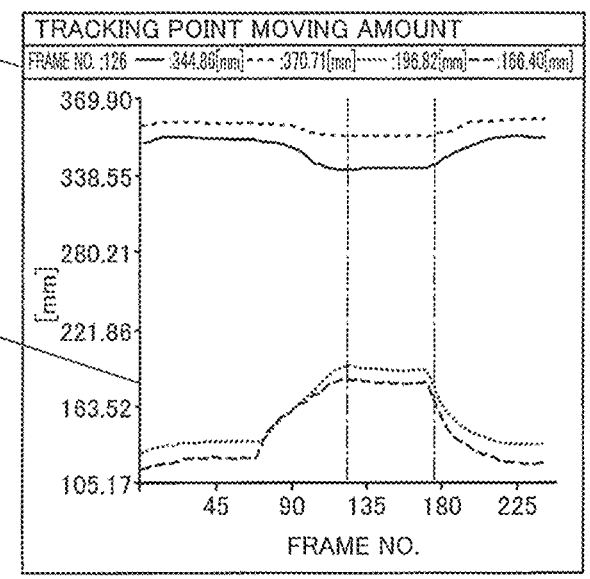
FIG. 41A, FIG. 41B and FIG. 41C are diagrams illustrating part of a display screen of the radiation image display apparatus according to the associated technique.
Figure 41B:
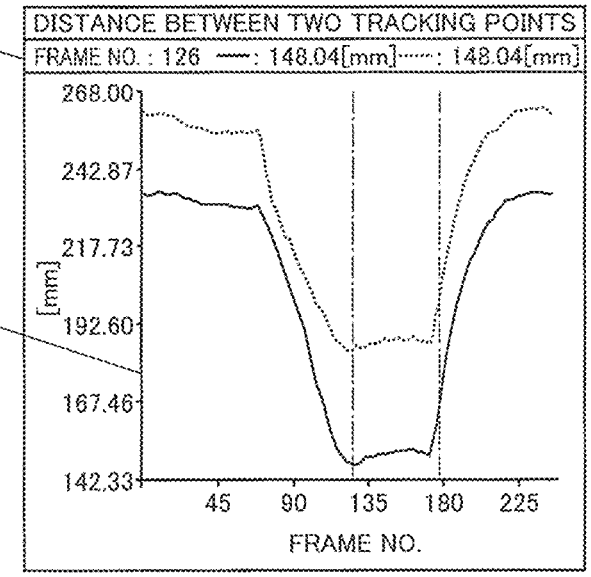
Figure 41C:
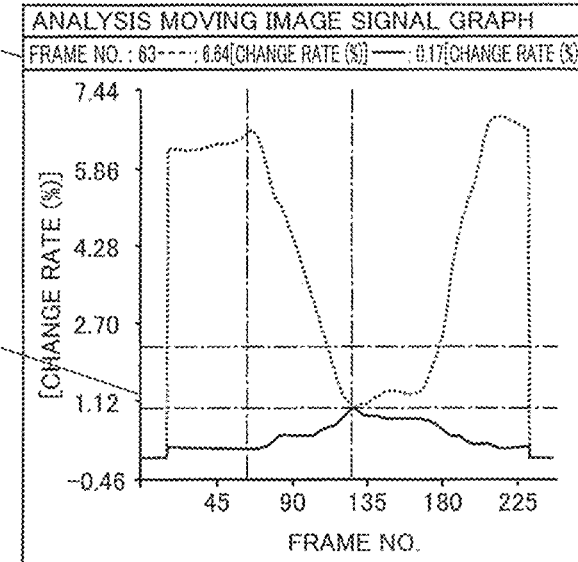

In view of such a problem, as shown, for example, in FIG. 41A, FIG. 41B and FIG. 41C, information M of various measurement results may be displayed in numerical values together with a graph G. There are various graphs G showing "original image average signal value," "tracking point moving amount," "distance between two tracking points," "analysis signal value" or the like, all of which can be handled.

Figure 42:
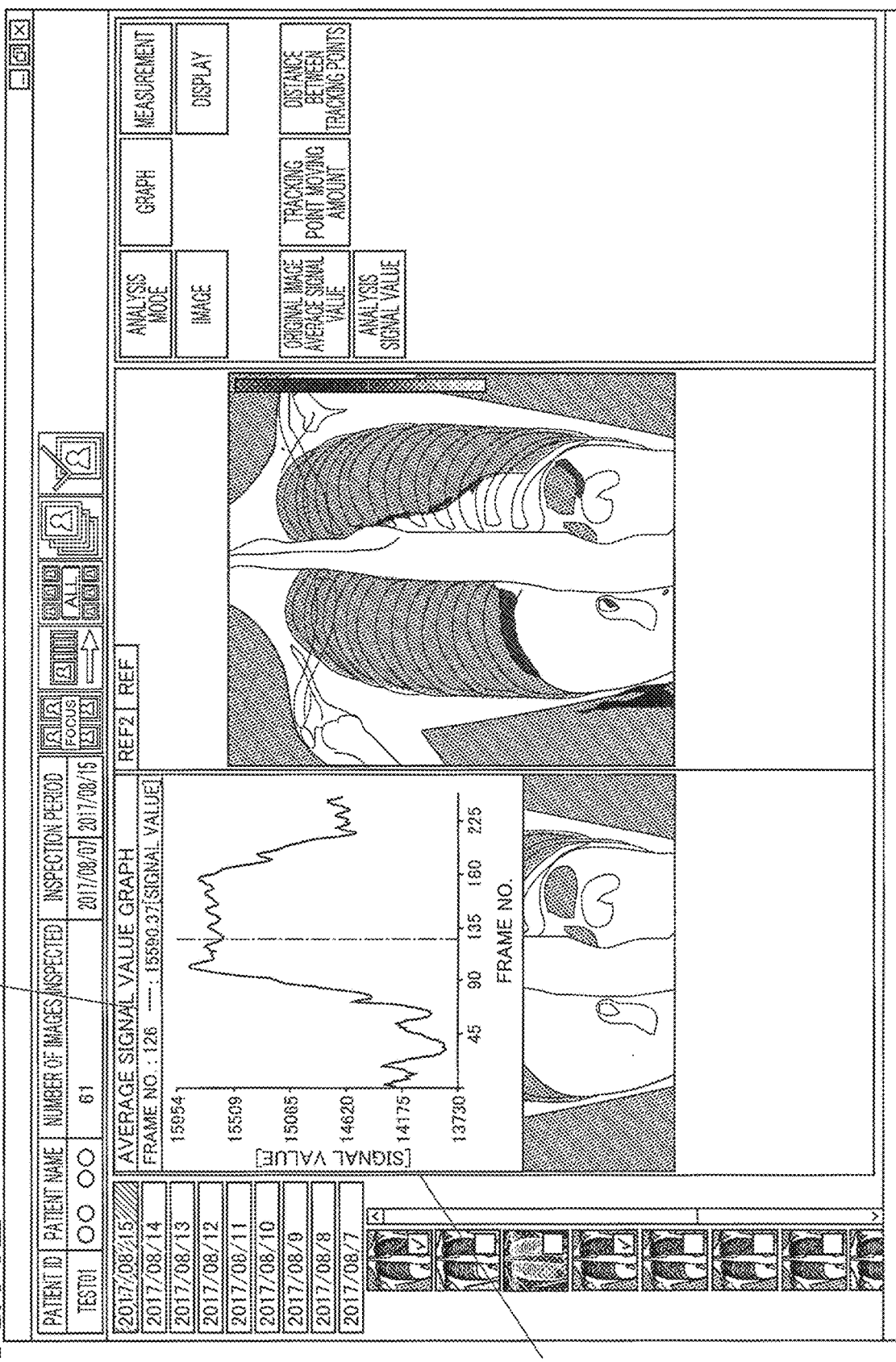
FIG. 42 shows an example of a display screen of the radiation image display apparatus according to the associated technique.
Figure 43:
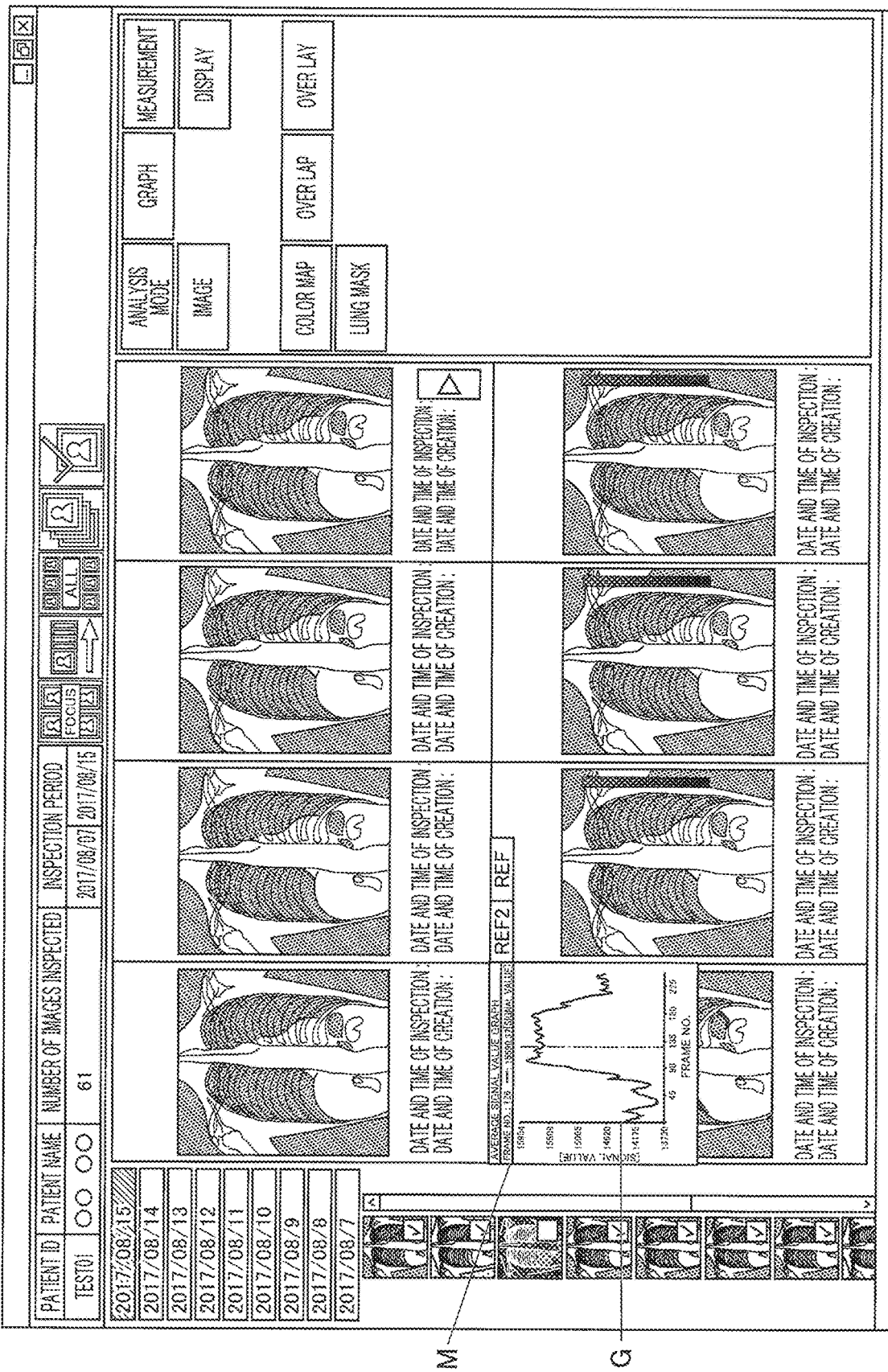
FIG. 43 shows an example of a display screen of the radiation image display apparatus according to the associated technique.

Note that the position at which and the size in which the graph G and the information M of measurement results are displayed can be changed according to the number of frames of the dynamic images Io, Ia and Ip displayed as shown, for example, in FIG. 42 and FIG. 43.

By displaying the measurement results together with the graph G in this way, it is possible to facilitate visual recognition.

Furthermore, when diagnosing a certain disease using dynamic images, it may be sometimes desirable to quickly confirm only measurement results based on the dynamic images without referring to the dynamic images.

Figure 44:
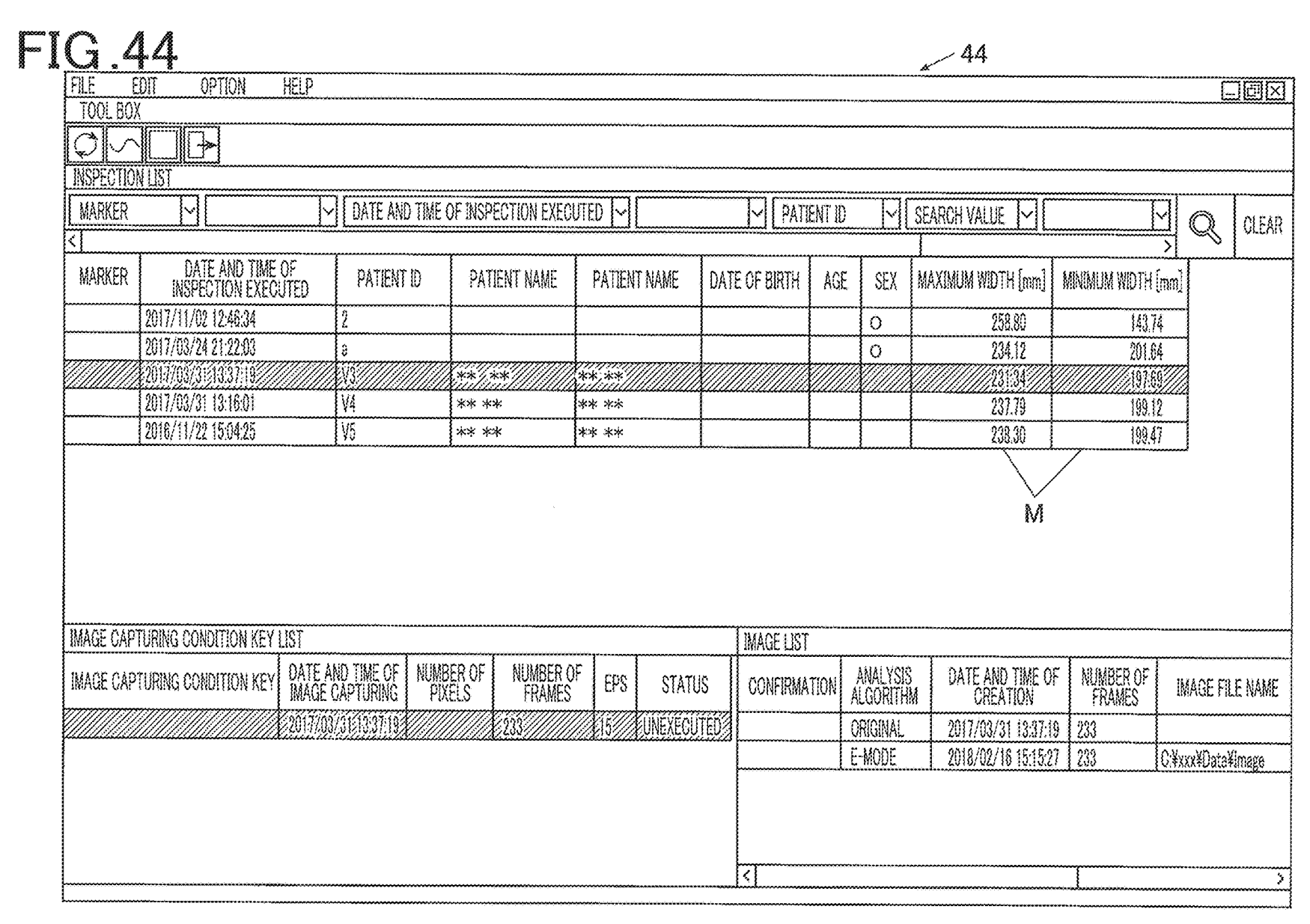

Therefore, it may be possible to display thumbnail images of graphs in an inspection list or display measurement results M (maximum/minimum width or the like) together with the inspection information (date and time of inspection, patient ID or the like) in a list as shown, for example, in FIG. 44.

By so doing, when it is desirable to confirm only the measurement results M, it is possible to omit display of dynamic images.

Displaying the measurement results in a list makes it possible to facilitate comparisons.

[Selection of Target Patient]

Furthermore, when diagnosing a certain disease using dynamic images, it may be sometimes desirable to compare symptoms with another patient having the same disease.

Therefore, the radiation imaging system may be provided with an interface for registering diseases and a database for managing patient names, diseases, image data of captured dynamic images or the like in association with one another and may be enabled to display dynamic images of the other patient having the same disease as related dynamic images.

Figure 45:
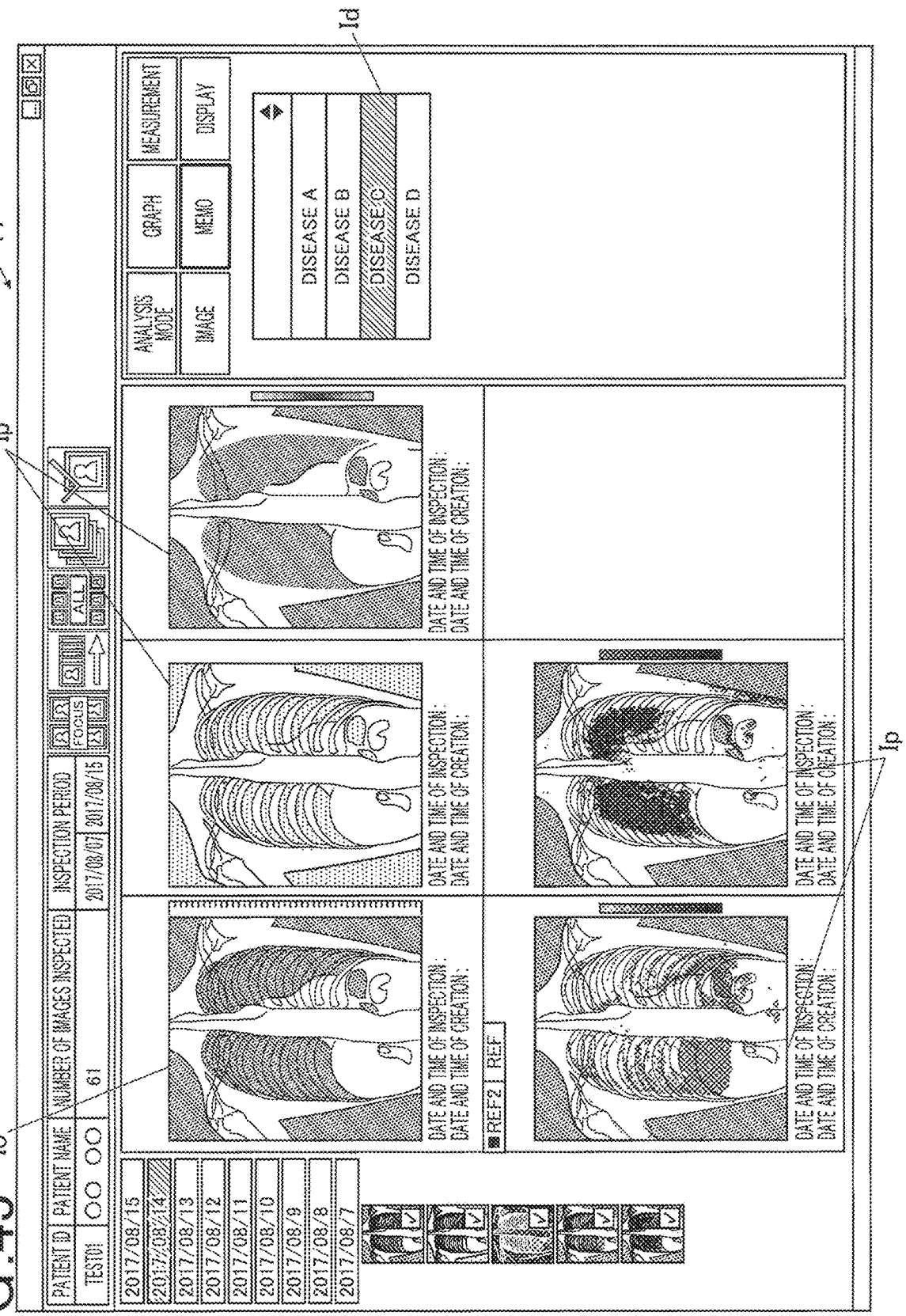
FIG. 45 shows an example of a display screen of the radiation image display apparatus according to the associated technique.

More specifically, as shown, for example, in FIG. 45, an icon Id of a disease may be displayed, and by selecting an icon Id of a certain disease, dynamic images of the other patient having the selected disease may be displayed.

By so doing, it is possible to compare with another patient having the same disease.

[Deletion of Analysis Dynamic Image]

In the radiation imaging system that handles dynamic images, the data amount becomes enormous and this presses storage capacity, and it is therefore necessary to delete unnecessary image data.

In such a case, image data may be preferably deleted in descending order of date of creation. Furthermore, when there are a plurality of pieces of image data having the same or close date of creation, image data may be preferably deleted in order from analysis dynamic images Ia (other than original dynamic image Io).

If an original dynamic image Io is left behind, an analysis dynamic image Ia can be generated again from the original dynamic image Io, and by so doing, it is possible to secure more image data while preventing oppression of storage capacity or the like.

Although embodiments of the present invention have been described and illustrated in detail, the disclosed embodiments are made for purposes of illustration and example only and not limitation. The scope of the present invention should be interpreted by terms of the appended claims.

What is claimed is:

1. A radiation image display apparatus comprising:
a displayer; and
a display controller that displays, on the displayer, a dynamic image constituted of a plurality of frame images and a graph corresponding to the dynamic image,
wherein the display controller displays, on the graph, frame information of the frame images displayed on the displayer,
wherein the graph is a graph in which an horizontal axis indicates frame numbers, and the display controller displays, on the graph, a longitudinal line corresponding to the frame numbers,
the radiation image display apparatus further comprises an operating part that receives a user operation of moving the longitudinal line, and
the display controller displays, on the displayer, a frame image corresponding to a frame number at a point at which the longitudinal line crosses the horizontal axis.

2. The radiation image display apparatus according to claim 1, wherein the frame
information is information indicating frame numbers of the dynamic image.

3. The radiation image display apparatus according to claim 1, wherein the dynamic image includes at least one among an original dynamic
image, an analysis dynamic image obtained by applying predetermined image processing to image data of the original dynamic image, and a related dynamic image related to at least either the original dynamic image or the analysis dynamic image.

4. The radiation image display apparatus according to claim 3, wherein the display
controller displays, on the displayer, at least two among the original dynamic image, the analysis dynamic image, and the related dynamic image next to each other.

5. The radiation image display apparatus according to claim 3, wherein the display
controller plays back, as a moving image, at least one among the original dynamic image, the analysis dynamic image, and the related dynamic image.

6. The radiation image display apparatus according to claim 1, wherein the display
controller displays and plays back the dynamic image on the displayer.

7. The radiation image display apparatus according to claim 6, wherein the display
controller displays an icon for instructing playback of the dynamic image at a position where the icon and the graph do not overlap.

8. A non-transitory computer-readable storage medium storing a program that
causes a computer of a radiation image display apparatus including a displayer to:
display, on the displayer, a dynamic image constituted of a plurality of frame images and a graph corresponding to the dynamic image; and
display, on the graph, frame information of the frame images displayed on the displayer,
wherein the graph is a graph in which an horizontal axis indicates frame numbers, and the displayer displays, on the graph, a longitudinal line corresponding to the frame numbers,
the radiation image display apparatus further comprises an operating part that receives a user operation of moving the longitudinal line, and
the display controller displays, on the displayer, a frame image corresponding to a frame number at a point at which the longitudinal line crosses the horizontal axis.

9. A radiation imaging system comprising:
a radiation image analysis apparatus that can apply predetermined image processing to dynamic image data constituted of a plurality of frame images to generate analysis dynamic image data; and
the radiation image display apparatus according to claim 1.

* * * * *